United States Patent
Maniar et al.

(10) Patent No.: US 10,576,050 B2
(45) Date of Patent: Mar. 3, 2020

(54) METHODS AND COMPOSITIONS FOR TREATMENT OF CANCER

(71) Applicants: ONCONOVA THERAPEUTICS, INC., Newtown, NJ (US); THE TRUSTEES OF COLUMBIA UNIVERSITY IN THE CITY OF NEW YORK, New York, NY (US); Manoj Maniar, Fremont, CA (US); Azra Raza, New York, NY (US); Francois Wilhelm, Princeton, NJ (US)

(72) Inventors: Manoj Maniar, Fremont, CA (US); Azra Raza, New York, NY (US); Francois Wilhelm, Princeton, NJ (US)

(73) Assignee: ONCONOVA THERAPEUTICS, INC., Newtown, NJ (US)

(*) Notice: Subject to any disclaimer, the term of this patent is extended or adjusted under 35 U.S.C. 154(b) by 0 days.

(21) Appl. No.: 14/649,759

(22) PCT Filed: Dec. 6, 2013

(86) PCT No.: PCT/US2013/073667
§ 371 (c)(1),
(2) Date: Jun. 4, 2015

(87) PCT Pub. No.: WO2014/089483
PCT Pub. Date: Jun. 12, 2014

(65) Prior Publication Data
US 2015/0313859 A1     Nov. 5, 2015

Related U.S. Application Data

(60) Provisional application No. 61/826,973, filed on May 23, 2013, provisional application No. 61/734,933, filed on Dec. 7, 2012.

(51) Int. Cl.
| | | |
|---|---|---|
| *A61K 31/198* | (2006.01) | |
| *A61K 45/06* | (2006.01) | |
| *A61K 47/10* | (2017.01) | |
| *A61K 31/706* | (2006.01) | |
| *A61K 31/454* | (2006.01) | |
| *A61K 31/428* | (2006.01) | |
| *A61K 31/10* | (2006.01) | |

(52) U.S. Cl.
CPC ............ *A61K 31/198* (2013.01); *A61K 31/10* (2013.01); *A61K 31/428* (2013.01); *A61K 31/454* (2013.01); *A61K 31/706* (2013.01); *A61K 45/06* (2013.01); *A61K 47/10* (2013.01)

(58) Field of Classification Search
CPC ................ A61K 31/428; A61K 31/496; A61K 31/4035; A61K 31/198; A61K 45/06
See application file for complete search history.

(56) References Cited

U.S. PATENT DOCUMENTS

| | | | |
|---|---|---|---|
| 6,201,154 B1 | 3/2001 | Reddy et al. | |
| 6,359,013 B1 | 3/2002 | Reddy et al. | |
| 6,414,034 B1 | 7/2002 | Reddy et al. | |
| 6,486,210 B2 | 11/2002 | Reddy et al. | |
| 6,541,475 B2 | 4/2003 | Reddy et al. | |
| 6,548,553 B2 | 4/2003 | Reddy et al. | |
| 6,576,675 B1 | 6/2003 | Reddy et al. | |
| 6,599,932 B1 | 7/2003 | Reddy et al. | |
| 6,787,667 B2 | 9/2004 | Reddy et al. | |
| 6,833,480 B2 | 12/2004 | Reddy et al. | |
| 7,053,123 B2 | 5/2006 | Reddy et al. | |
| 7,056,953 B2 | 6/2006 | Reddy et al. | |
| 7,598,232 B2 | 10/2009 | Reddy et al. | |
| 2011/0201675 A1* | 8/2011 | Jimeno ................ | A61K 31/192 514/44 R |

(Continued)

FOREIGN PATENT DOCUMENTS

WO   PCT/US13/73667   4/2014

OTHER PUBLICATIONS

Kumar, C.C. Genes and Cancer, 2011, vol. 2, No. 2, pp. 95-107.*
Santini, V. The Oncologist, 2011, vol. 16, Suppl. 3, pp. 35-42.*
Pardanani et al. Hematologica, 2011, vol. 96, No. 1, pp. 8-10.*
Final phase I/II results of Rigosertib (ON01910.Na) hematological effects in patients with myelodysplastic syndrom and corrolation. Azra Raza et al, Abstact, Ash 2011.
ON01910.Na a non-ATP-competative small molecule inhibitor of plk1.Gumireddy K et al, Cancer Cell 7(3): 275-86, 2005.
Highlights from the NIH state of science symposium on myelodysplastic syndromes. 2011.
Design, synthesis and biological evaluation of E-styrylbenzylsulfones as novel anticancer agents. Reddy MV et al, J.Med.Chem.10 (51):86-100, 2008.

(Continued)

*Primary Examiner* — Samira J Jean-Louis
(74) *Attorney, Agent, or Firm* — Law Offices of Khalilian Sira, LLC; Houri Khalilian

(57) ABSTRACT

The invention discloses a method of treating cancer refractory to an anticancer agent comprising administering to a cancer patient a pharmaceutical composition comprising at least one compound of Formula 1

Formula 1

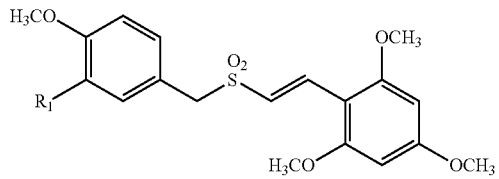

Figure 1A:
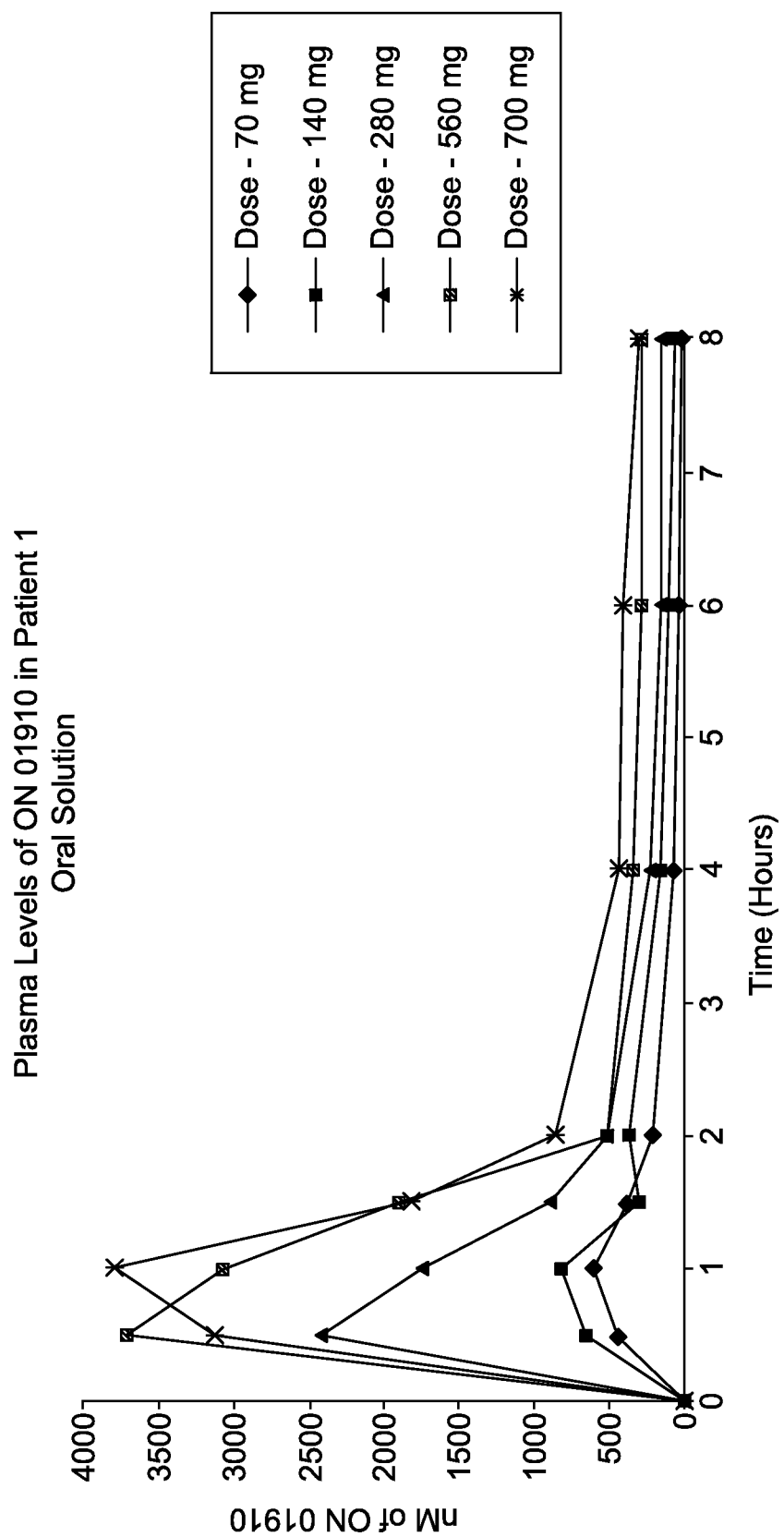

Where $R_1$ is selected from the group consisting of —$NH_2$, —NH—$CH_2$—COOH, —NH—CH($CH_3$)—COOH, —NH—C($CH_3$)$_2$—COOH, —NH—$CH_2$—$CH_2$—OH and —N—($CH_2CH_2OH$)$_2$ or a pharmaceutically acceptable salt of such a compound, and an anticancer agent.

10 Claims, 16 Drawing Sheets

(56) References Cited

U.S. PATENT DOCUMENTS

2014/0120083 A1* 5/2014 Stern ............ A61K 31/00 424/133.1

OTHER PUBLICATIONS

Clinical activity and safety of the dual pathway inhibitor Rigosertib for higher risk myelodysplastic syndromes. Silverman LR et al, Hematol.Oncol. 33(2):57-66,2015.

Phase I clinical trial of oral Rigosertib in patients with myelodysplastic syndromes. Komrokji RS et al, Hematol.162(4):517-24, 2013.

A phase II/III randomized study to compare efficacy and safety of Rigosertib plus gemcitabine versus gemcitabine alone. O'Neil BH et al, Ann.Oncol.26(9):1923-9,2015.

Phase I dose escalation study of Rigosertib by 2,4, or 8 hour infusion twice weekley in patients with advanced cancer. Advani SH et al, Indian J. Cancer, 51(1):40-4, 2014.

The dual pathway inhibitor Rigosertib is effective in direct patient tumor xenogrfts of head and neck squamous cell. Anderson RT et al, Mol.Cancer Ther.12(10):1994-2005,2013.

Phase I study of intravenous Rigosertib (ON01910.Na) a novel styrylbenzylsulfone structure producing G2/M arrest. Ohnuma T et al, Am.J.Cancer Res. 20(3):323-38, 2013.

Ran GTPase activating protein lis a therapeutic target in diffuse large B-cell lymphoma. Kung Chao Chang et al, PLOS 1, 8(11):2013.

Phase 1 study of ON01910.Na (Rigosertib), a multikinase p13k inhibitor in relapsed/refractory B-cell malignancies. Roschewski M et al, Leuk. 27(9)1920-3, 2013.

Directed therapy for patients with myelodysplastic syndroms by suppression of cyclin D1 with ON01910. Na. Olnes MJ et al, Leuk. Res. 36(8): 982-9, 2012.

Phase 1 study of Rigosertib, an inhibitor of phosphatidylinositol 3-kinase and polo-like kinase 1 pathways. Ma W W et al, Clin. Cancer Res.18(7):2048-55, 2012.

Treatment of higher risk myelodysplastic syndrom patients unresponsive to hypomethylating agents with ON 01910.Na. Seetharam M et al, Leuk. Res.36(1):98-103, 2012.

Discovery of a clinical stage multikinase inhibitor. Ramana Reddy MV, et al, J.Med. 54:6254-6276, 2011.

Deletion of the transcription factor IKaros in myeloproliferative neoplasms. R JA Gerl et al, Leuk.1-9, 2010.

New therapeutics for myelodysplastic syndromes. List Alan F. Leuk.Res,36:1470-1474, 2012.

A phase I study to access oral bioavailability of a novel oral soft gelatin capsule formulation of Rigosertib. Raza Azra et al, J.Clin. Oncol. ASCO Abstract, 2012.

Failure of hypomethylating agent-based therapies in myelodysplastic syndromes. Kadia Tapan M et al, semin.Oncol.38:682-692, 2011.

* cited by examiner

METHODS AND COMPOSITIONS FOR TREATMENT OF CANCER

This application claims priority to U.S. Provisional Application No. 61/734,933, filed Dec. 7, 2012; U.S. Provisional Application No. 61/826,973, filed May 23, 2013; and PCT Patent Application No. PCT/US13/73667, filed Dec. 6, 2013, the entire contents of each of which are incorporated herein by reference.

FIELD OF THE INVENTION

The invention relates to methods and composition for the treatment of cancer. Specifically the methods and compositions of the invention are directed to treatment of diseases related to bone marrow neoplasm in particular refractory hematological cancers.

I. BACKGROUND OF THE INVENTION

A significant number of tumors are classified as poorly or non-responsive to therapeutic drugs or radiotherapy. Increasing the chemotherapeutic dosage or radiation dose not only fails to improve the therapeutic response, but also contributes to the development of side effects and resistance to therapy. A great deal is now known about mechanisms of drug resistance in cancer cells. Despite the development of new targeted anticancer therapies, mechanisms that protect cells against cytotoxic compounds in mammals will continue to act as obstacles to successful treatment of cancer.

The design of cancer chemotherapy has become increasingly advanced in the last few years, yet there is no cancer treatment that is 100% effective against cancer mainly because of development of resistance to the anticancer drug. Resistance to treatment with anticancer drugs results from a variety of factors including individual variations in patients and somatic cell genetic differences in tumors. Frequently resistance is intrinsic to the cancer, but as therapy becomes more and more effective, acquired resistance has also become common. The most common reason for acquisition of resistance to a broad range of anticancer drugs includes expression of one or more energy-dependent transporters that detect and remove anticancer drugs from cells. Insensitivity to drug-induced apoptosis and induction of drug-detoxifying mechanisms are among other reasons underlying acquired anticancer drug resistance.

Studies on mechanisms of cancer drug resistance have yielded important information about how to circumvent resistance and to improve cancer chemotherapy and have provided additional knowledge for pharmacokinetics of many commonly used drugs. An ideal strategy would consist of the identification of anticancer agents able to act synergistically with standard treatments such as radiotherapy and chemotherapy and triggering the cell death preferentially in tumor cells.

Bone marrow malignancies are clonal disorders resulting from neoplastic transformation of hematopoietic stem or progenitor cells. Similar to their normal counterparts, transformed blood-forming cells remain dependent on signals from the hematopoiesis-regulating stromal environment for survival and proliferation. A review of the literature on stromal abnormalities in the leukemias, the myelodysplastic syndromes, and multiple myeloma reveals three principal mechanisms by which stromal derangements can contribute to the evolution of a neoplastic disease. In the simplest case, neoplastic blood-forming cells induce reversible changes in stroma function or composition which result in improved growth conditions for the malignant cells. In the second setting, functionally abnormal end cells derived from the malignant clone become an integral part of the stroma system, selectively stimulating the neoplastic cells and inhibiting normal blood cell formation. In the third condition, the emergence of a neoplastic cell population is the consequence of a primary stroma lesion characterized by inability to control regular blood cell formation (malignancy-inducing microenvironment).

The WHO classification system for hematopoietic tumors recognizes five categories of myeloid malignancies, including acute myeloid leukemia (AML), Myelodysplastic Syndrome (MDS), Myeloproliferative Neoplasm (MPN), MDS/MPN overlap, and PDGFR/FGFR1-rearranged myeloid/lymphoid neoplasms with eosinophilia. MDS and MPN are two groups of diseases in the family of bone marrow malignancies. MDS and MPN are not single diseases, but each encompasses a collection of hematopoietic and stem cell disorders.

The myelodysplastic syndromes, formerly known as preleukemia, are a diverse collection of hematological medical conditions that involve ineffective production (or dysplasia) of the myeloid class of blood cells. The WHO MDS category of diseases includes refractory anemia (RA), refractory anemia with ringed sideroblasts (RARS), refractory anemia with excess blasts (RAEB), refractory anemia with excess blasts in transformation (RAEB-T), and chronic myelomonocytic leukemia (CMML). Patients with MDS often develop severe anemia and require frequent blood transfusions. In most cases, the disease worsens and the patient develops cytopenias (low blood counts) caused by progressive bone marrow failure. In about one third of patients with MDS, the disease transforms into acute myelogenous leukemia (AML), usually within months to a few years.

Hematopoietic cell diseases are thought to arise from mutations in the multi-potent bone marrow stem cell, but the specific defects responsible for these diseases remain poorly understood. Differentiation of blood precursor cells is impaired, and there is a significant increase in levels of apoptotic cell death in bone marrow cells. Clonal expansion of the abnormal cells results in the production of cells which have lost the ability to differentiate. In MDS, if the overall percentage of bone marrow myeloblasts rises over a particular cutoff (20% for WHO classification, 30% for FAB classification) then transformation to acute myelogenous leukemia (AML) is said to have occurred. The progression of MDS to AML is a good example of the multi-step theory of carcinogenesis in which a series of mutations occur in an initially normal cell and transform it into a cancer cell.

While recognition of leukemic transformation was historically important, a significant proportion of the morbidity and mortality attributable to MDS results not from transformation to AML but rather from the cytopenias seen in all MDS patients. The myelodysplastic syndromes are all disorders of the stem cell in the bone marrow. In MDS, hematopoiesis is disorderly and ineffective. The number and quality of blood-forming cells decline irreversibly, further impairing blood production. Anemia is the most common cytopenia in MDS patients. The two most serious complications in MDS patients resulting from their cytopenias are bleeding (due to lack of platelets) or infection (due to lack of white blood cells). Long-term transfusions of packed red blood cells lead to iron overload, among other clinical risks.

The recognition of epigenetic changes in DNA structure in MDS has shown that proper DNA methylation is critical in the regulation of proliferation genes, and the loss of DNA methylation control can lead to uncontrolled cell growth, and cytopenias. The recently approved DNA methyltransferase inhibitors take advantage of this mechanism by creating a more orderly DNA methylation profile in the hematopoietic stem cell nucleus, and thereby restore normal blood counts and retard the progression of MDS to acute leukemia.

Every year, between 15,000 and 45,000 patients in the US are diagnosed with MDS (Goldberg et al., 2010; Rollison et al., 2006). The age at which most patients are diagnosed is between 60 and 75 years old. Survival of patients with MDS is dependent on the severity of their disease; on average, it is 3 to 5 years after initial diagnosis (Ma et al., 2007). Most patients succumb to complications of cytopenias (uncontrollable bleeding or infections) or because the disease progresses to AML. Cases of AML that arise from prior MDS do not respond well to chemotherapy and have a poor prognosis.

There have also been many cases of MDS/MPN overlap. MDS/MPN overlap disorders come in many variations: as a true overlap condition at initial presentation, with evidence of dysplasia of cellular elements and myeloproliferative components (such as fibrosis, hypercellularity, or organomegally); as MDS that takes on MPN features over time; or, conversely, as an MPN in which progressive marrow dysplasia develops. These disorders include chronic myelomonocytic leukemia (CMML), atypical (BCR-ABL1 negative) chronic myeloid leukemia, juvenile myelomonocytic leukemia, and MDS/MPNu1 as seen in this patient. Some MDS/MPN cases have JAK2 mutations (such as the provisional entity, refractory anemia with ring sideroblasts and thrombocytosis). The proliferative components of these disorders are related to abnormalities in the RAS/MAPK signaling pathways, and approximately 50 percent are associated with TET2 mutations.

While investigational drug therapies exist, there is currently not a curative drug treatment for most hematological cancers. Current treatment strategies for hematopoietic cancers include:

1) Allogeneic stem cell transplantation. This, however, is not a good treatment option for patients with lower-risk MDS because it usually shortens their survival. This treatment is generally reserved for patients 55 years and younger with more severe disease and who can withstand the rigors of the procedure. Although bone marrow transplant has resulted in long-term disease-free survival in some patients with MDS, the morbidity and mortality of this approach remains high. Many patients are not candidates for such an approach because of their age or other health issues. While bone marrow transplantation clearly has a role in the treatment of MDS, the decision to proceed to transplantation is not always easy and the optimal approach has not been clearly defined (Luger and Sacks, 2002).

2) Chemotherapy. These therapies result in severe reactions in the patients which lead to resistance to the therapy.

3) Erythropoiesis-stimulating agents (ESAs): ESAs encourage the body to make more red blood cells. ESAs have been used in managing anemia in MDS patients. However, recent data has raised safety concerns with the use of ESAs in oncology (Bennett et al, JAMA, 2008, 299, 914). The U.S. Food and Drug Administration has not approved ESAs for MDS because of the lack of randomized clinical studies and concerns about ESA safety of in patients with solid tumors, such as breast cancer or lung cancer. But research has not shown that these drugs increase the risk of AML in MDS, and they may improve survival. The work is currently in progress to investigate clinical reasons as to why some patients respond to ESAs for a while, but then have a relapse.

4) Blood transfusion. Anemia is a common occurrence in MDS patients, with more than 50% patients exhibiting anemia when first diagnosed with MDS. Up to 90% will develop anemia during progression of the disease and 80% will require transfusions to control the disease process. Chronic red blood transfusions to treat anemia generally result in iron overload, which is damaging to heart, liver and other tissues. Symptoms go unnoticed until serious organ damage occurs resulting in hepatic failure, heart disease and bone marrow suppression. Chronic transfusion dependency and iron overload are independent predictors of decreased survival and increased transformation to acute myeloid leukemia (AML).

5) DNA methyltransferase inhibitors. Hypomethylating agents or demethylating, agents, for example azacytidine (Vidaza®), decitabine (Dacogen®) and the 5q31 clone suppressor lenalidomide (Revlimid®), help the bone marrow of patients with hematopoietic cancers to function normally and kill unhealthy cells. The most common adverse events associated with DNA Methyltransferase inhibitors are injection-site reactions, gastrointestinal events and hematologic events. Other adverse reactions included diarrhea, nausea and vomiting. Currently, several other new agents are under investigation for the treatment of hematological cancers. These include HDAC inhibitors (phenyl butyrate, valproic acid, MS-275, MGCD0103, vorinostat); Farnesyltransferase inhibitors (topifarnib, lonifarnib); TNF inhibitor Embrel®, nucleoside analogs, retinoids and glutathione derivatives.

The most important goals in hematopoietic cancers, in addition to prolonging survival, are development of higher hematologic responses and improvement in quality of life. Since hematopoietic cancers are biologically complex heterogeneous diseases, a single treatment strategy may not work for all patients. Accordingly, none of the aforementioned therapies are curative, and patients ultimately fail to respond over time. This failure of response leads to a poor prognosis where the average life expectancy is within few months. Thus, there is an urgent need for new treatments for patients with hematopoietic and/or hematological cancer, whose disease no longer responds to the existing drugs. Development of new treatment strategies including effective combination therapies has become critical in cancer treatment.

Accordingly, there is a long felt need in discovering new treatment strategies that might be effective in people with hematological cancer. Because of a lack of available treatments for myelodysplastic syndrome and acute myeloid leukemia, and the toxicity and side effects associated with existing agents, the need exists for new therapies in the treatment of these diseases, particularly therapies that have greater potency and lower toxicity and/or activity across a broader spectrum of cell types.

The present invention as disclosed and described herein provides therapeutic methods and compositions that can be used in combination with chemotherapy or radiotherapy to treat or ameliorate symptoms of hematological cancers such as MDS, and/or prolonged survival of cancer patients.

II. SUMMARY OF THE INVENTION

The invention as claimed herein provides compositions and methods for treatment of cancer. In a preferred embodiment the method of the invention provides treatment to cancers that are refractory to anticancer agents. The pharmaceutical composition of the invention comprises at least one compound of Formula 1

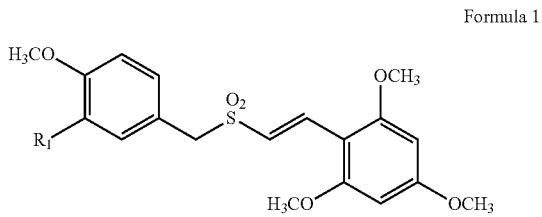

Formula 1

Where $R_1$ is selected from the group consisting of —$NH_2$, —NH—$CH_2$—COOH, —NH—CH($CH_3$)—COOH, —NH—C($CH_3$)$_2$—COOH, —NH—$CH_2$—$CH_2$—OH and —N—($CH_2CH_2OH$)$_2$ or a pharmaceutically acceptable salt of such a compound, and an anticancer agent.

According to one embodiment, the $R_1$ group of the compound of Formula 1 is —NH—$CH_2$—COOH.

In a preferred embodiment, the compound of Formula 1 is Rigosertib represented herein by Formula 1 A

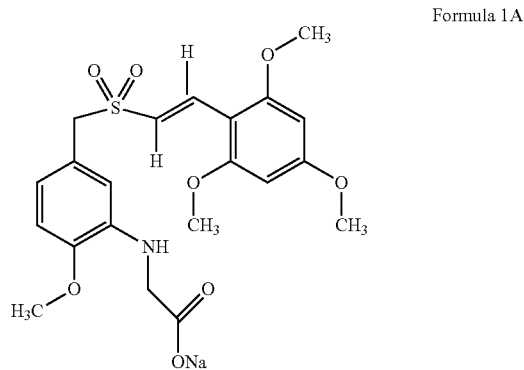

Formula 1A

In one embodiment, administration of the compound of Formula 1 is prior to, concomitant with, and/or subsequent to the administration of the anticancer agent.

The administration of Rigosertib to cancer patients removes the effect of anticancer drug resistance and can be administered to patients after the original therapy has been completed, in some occasions about 1, 9, or 30 weeks after completion of therapy with the anticancer agent. The number of weeks recited after completion of therapy also includes specific integer amounts between the recited numbers. For example, about 1, 9, or 30 weeks after completion of therapy also includes 2, 3, 4, 5, 6, 7, 8, 10, 15, 20, and 25 weeks and any integer values thereof.

The anticancer agent includes, by way of example and not limitation, cytotoxic agents, chemotherapeutic agents comprising alkylating agents, antimetabolites, anthracyclines, alkaloids, topoisomerase inhibitors, monoclonal antibodies; erythropoiesis modulating agents comprising ESAs including EPO (endogenous, recombinant and/or synthetic EPO), epoetin alfa, Procrit, Epogen, epoetin beta, darbepoetin alfa, and/or methoxy polyethylene glycol-epoetin beta; DNA methyltransferase inhibitors comprising azacitidine, decitabine, and/or immunomodulators comprising lenalidomide, among others.

The compounds of the invention can be administered orally, intravenously, or both.

According to a preferred embodiment of the invention the compound of Formula 1 is Rigosertib and the anticancer agent comprises ESA. The invention, as disclosed and described herein, provides data showing surprisingly that MDS patient refractory to ESA can be successfully treated with Rigosertib in combination with ESA. In another embodiment, ESA can be administered prior to, or subsequent to the administration of Rigosertib.

The anticancer agent of the invention further comprises one or more DNA methyltransferase inhibitors that can also be administered prior to, concomitant with or subsequent to the administration of Rigosertib. In one embodiment, the DNA methyltransferase inhibitors comprise azacitidine, decitabine, or both and the anticancer agent further comprises linolidomide.

The cancer is defined broadly within the scope of the invention and it includes both hematological cancer and solid tumors. In one embodiment, the hematological cancer comprises MDS, MPN, or both. Rigosertib is administered to MDS patients who had previously failed treatment with azacitidine or decitabine, according to the following treatment schedules:

i) about 800 mg Rigosertib for three to five days every other week;

ii) about 650 mg to 1,700 mg Rigosertib for three to six days every other week;

iii) about 800 mg to 1,500 mg Rigosertib for two days every week for three weeks followed by one week without treatment; or iv) about 1,800 mg Rigosertib for three days every other week, wherein the patients experienced about 50% decrease in immature bone marrow cells, and median survival with Intermediate-1 risk MDS patients was about 77 weeks and for Intermediate-2 risk MDS patients about 37 weeks.

In one embodiment, Rigosertib is formulated in a 25 mg dose capsule and its oral administration in MDS patients has shown a plasma peak level of at least 2-4 µM with a plasma half-life of about 10±0.5 hours.

In another embodiment, Rigosertib is administered through continuous IV infusions over 24 hours to Patients with relapsed or refractory AML or transformed MPN with a fixed dose of 2400 mg/day either for 72 hours or 120 hours every other week using a standard dose escalation scheme.

In yet another embodiment Rigosertib is administered via a single-dose, three-treatment, and in three-period of sequential administration to MDS patients under fasting conditions in an intravenous dose of 800 mg over 24 hours and oral dose of 560 mg under fasting conditions.

According to one embodiment, a method of treating or ameliorating one or more symptoms of a hematological cancer refractory to an anticancer agent is disclosed. The method comprises administering Rigosertib to a cancer patient demonstrating symptoms including refractory anemia and excess blasts (RAEB), cytopenia, multi-lineage dysplasia, reduced erythrocyte and/or platelet count, reduced hemoglobin concentration, or any combination thereof.

In another embodiment, the anticancer agent comprises one or more hypomethylating agents, ESA or any combination thereof.

In yet another embodiment, the hematological cancer is MDS and patients are Low-Int-1 Risk transfusion dependent patients, wherein Rigosertib is administered orally according to an intermittent dosing schedule and the therapy achieved transfusion independence in about 50% of the transfusion dependent lower risk MDS patients.

According to one aspect, the invention provides an oral formulation of Rigosertib comprising 280 mg ON 01910.Na dissolved in about 62-72% PEG 400, 0-5% PEG 4000 and 0-5% purified water.

In another aspect, the invention provides an oral formulation of Rigosertib comprising 70 mg ON 01910.Na dissolved in 930 mg of PEG 400.

In yet another aspect, Rigosertib is administered orally with an intermittent dosing schedule of 560 mg/280 mg morning and afternoon, respectively for a period of 2-3 weeks.

These and other aspects, features and advantages of the present invention will become apparent after a review of the following detailed description of the disclosed embodiments and the appended claims.

III. BRIEF DESCRIPTION OF THE DRAWINGS

Figure 1B:
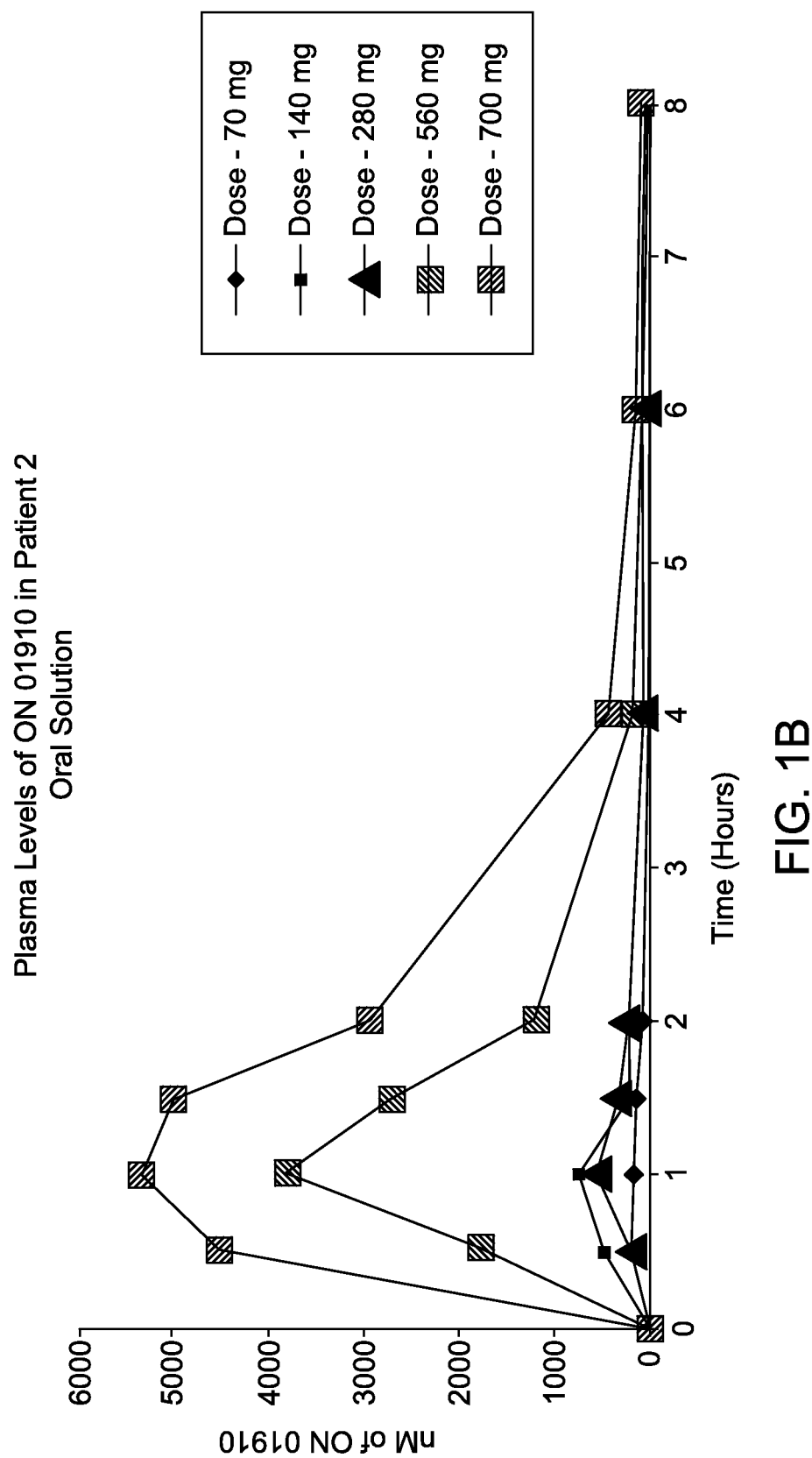
Figure 1C:
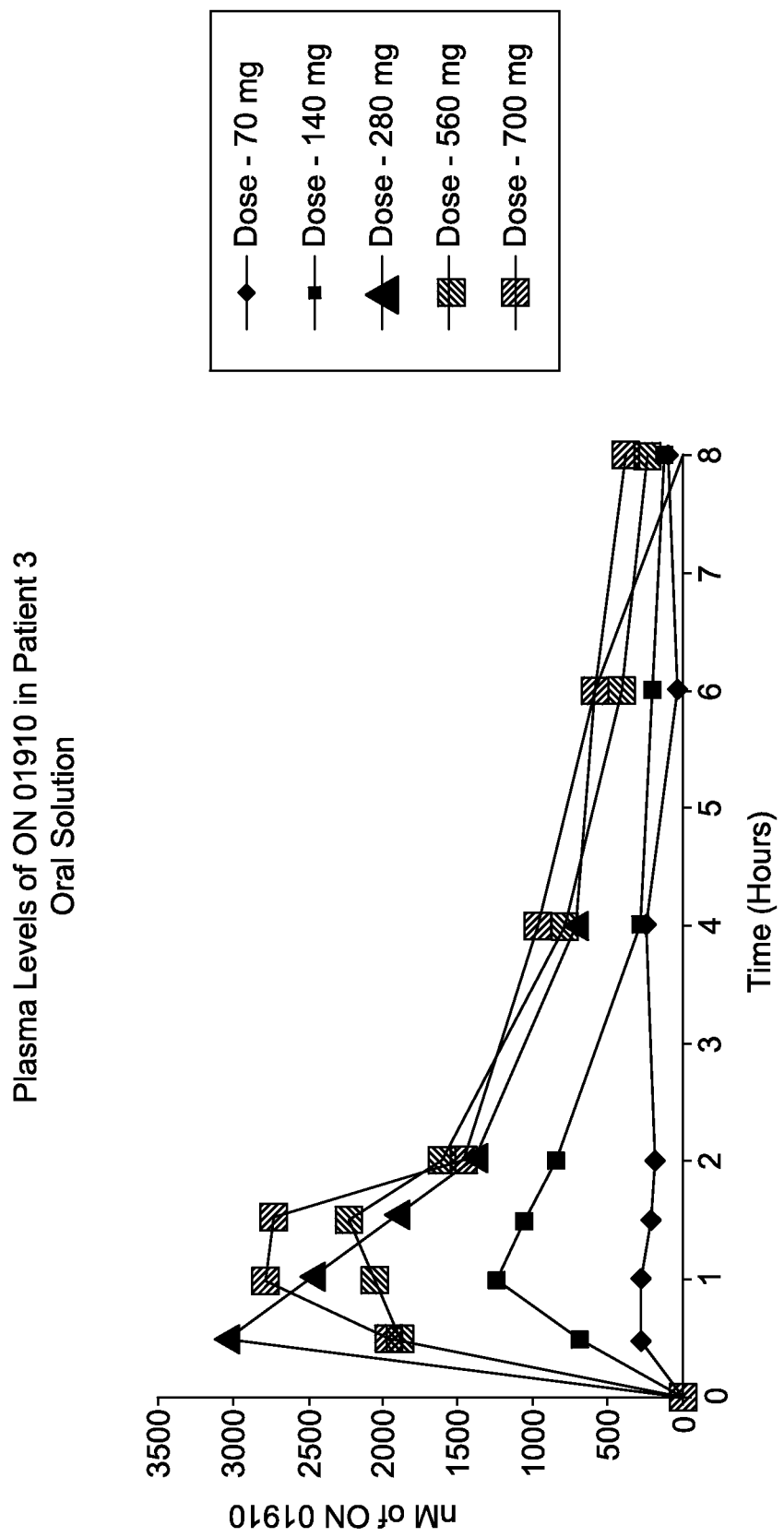

FIG. 1: Safety and efficacy of Rigosertib (ON 01910.Na) was determined in a dose escalation study in MDS patients refractory to ESA, lenalidomide and DNA Methyltransferase inhibitors. ESA was allowed as concomitant medication. The drug dose was escalated based on a defined escalation dose scheme (70 mg, 140 mg, 280 mg, 560 mg, and 700 mg). Three patients were treated with single escalating weekly doses of oral Rigosertib to determine the oral absorption of Rigosertib. Plasma concentrations as a function of time for the three patients are shown in FIGS. 1A, 1B and 1C, respectively, demonstrating that pharmacodynamically active concentrations were reached.

Figure 2:
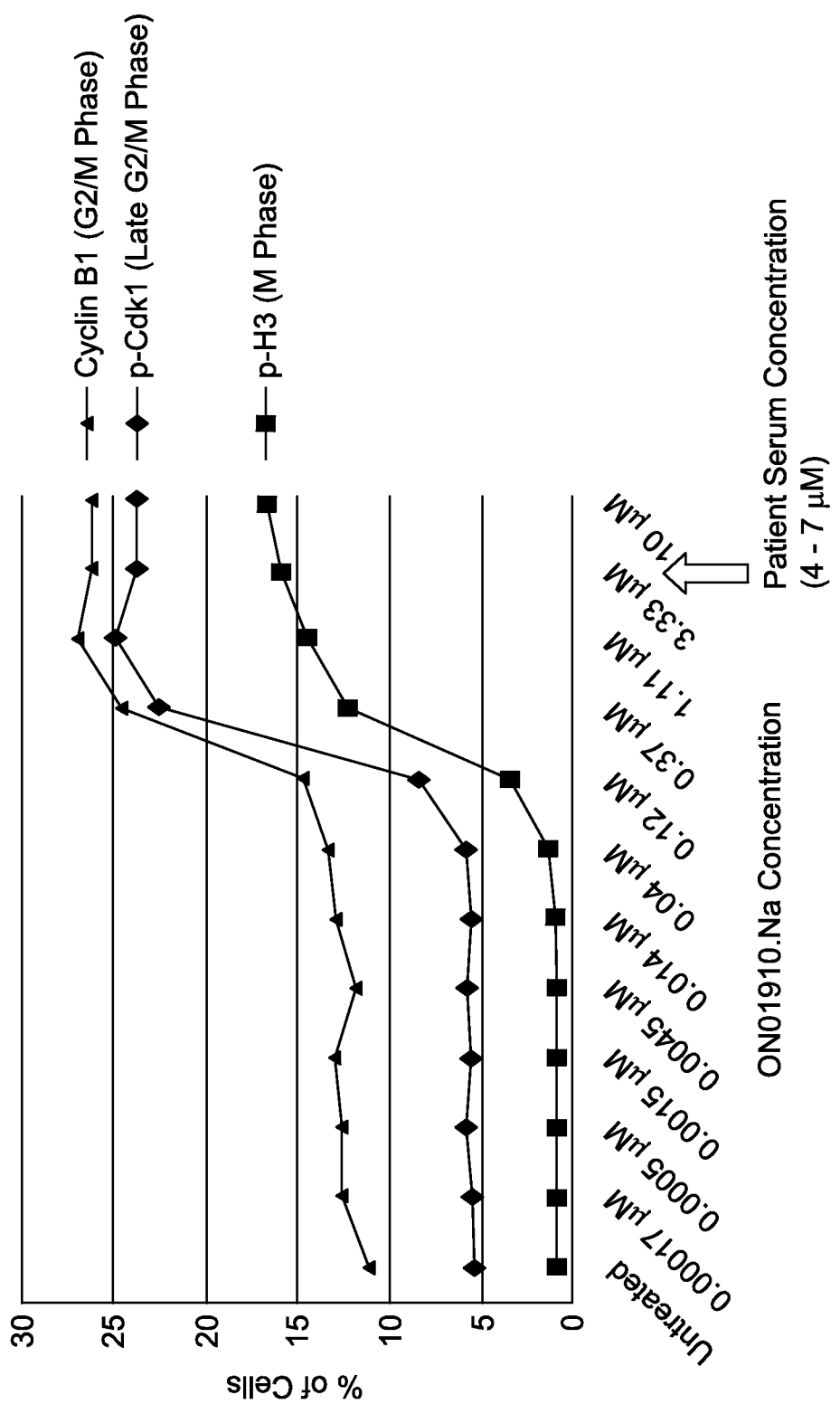

FIG. 2: In vitro effect of ON 01910.Na at clinically relevant concentrations on intracellular pathways in human GM-CSF-dependent erythroblastic TF-1 cell line using SCNP was evaluated in order to monitor transitional changes in the cell cycle, with a focus on the G2-M phase and to perform dose-dependent titrations of drug using these cell cycle readouts. The reagents chosen to measure cell cycle readouts were fluorochrome-conjugated antibodies that recognize cyclin B1, p-histone H3(S28) and p-Cdk1(Y15) and 4'6'-diamino-2-phenylindole (DAPI). The data show that at 24 hours after ON 01910.Na exposure there was a simultaneous increase in phosphorylation of histone H3(S28), a decrease in phosphorylation of Cdk-1(Y15), and accumulation of cyclin B1. ON 01910.Na exposure disrupted the G2/M cell cycle transition leading to mitotic arrest with subsequent apoptosis. TF-1 cell DNA content measured by DAPI verified this to be the case as increases in G2/M and sub-G1 (a measure of apoptotic cell death) were simultaneously observed. Maximal effects of ON 01910.Na on cell cycle signaling molecules were observed at a drug concentration of 0.37 µM and no further changes were seen at higher concentrations. These effects were also observed at 48 hours, although with more cell death. This assay was used to measure the pharmacodynamics activity of the drug in MDS patient samples pre- and post-treatment with ON 01910.Na.

Figure 3:
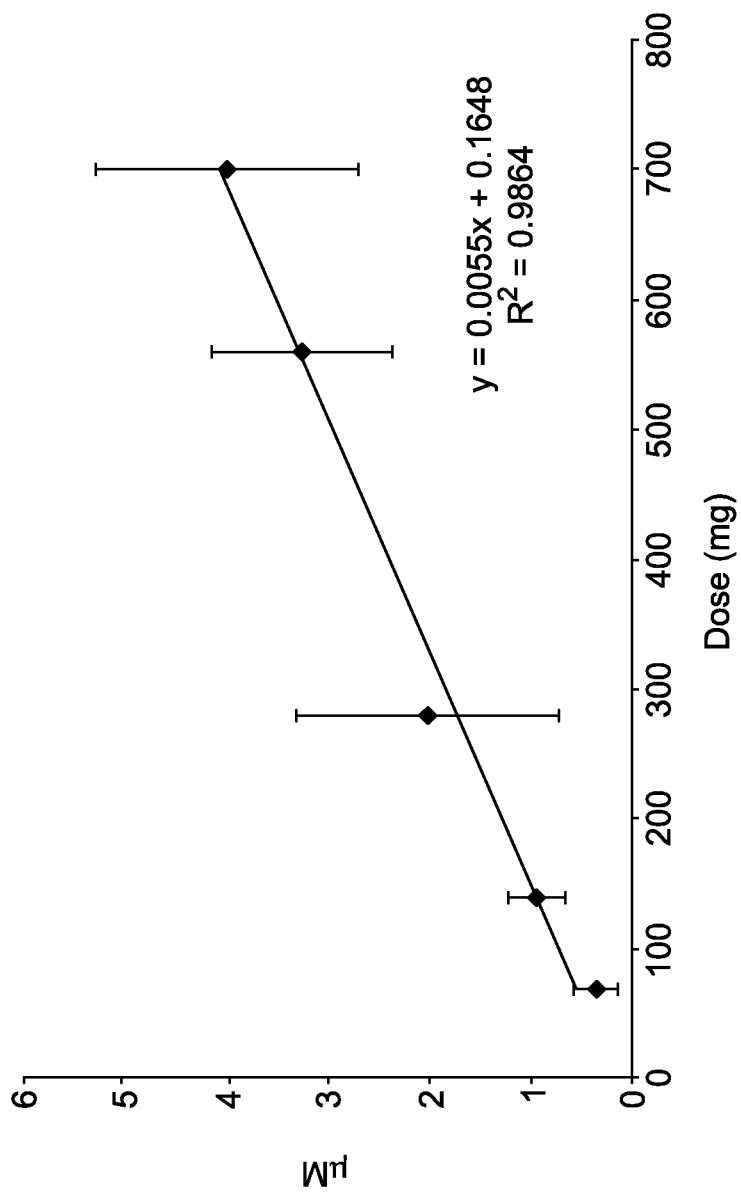

FIG. 3: The oral absorption and tolerability of Rigosertib administered as single weekly escalating doses in a fasting state were determined in 3 patients. All 3 patients received a 70 mg single oral dose and blood samples for pharmacokinetic analyses were obtained. In the absence of drug-related grade ≥2 toxicity, single dosing was escalated weekly in each patient to 140 mg (week 2), 280 mg (week 3), 560 mg (week 4) and 700 mg (week 5). The data shows that the drug concentration (Cmax) was dose dependent and increased linearly with each increasing dose of ON 01910.Na.

Figure 4:
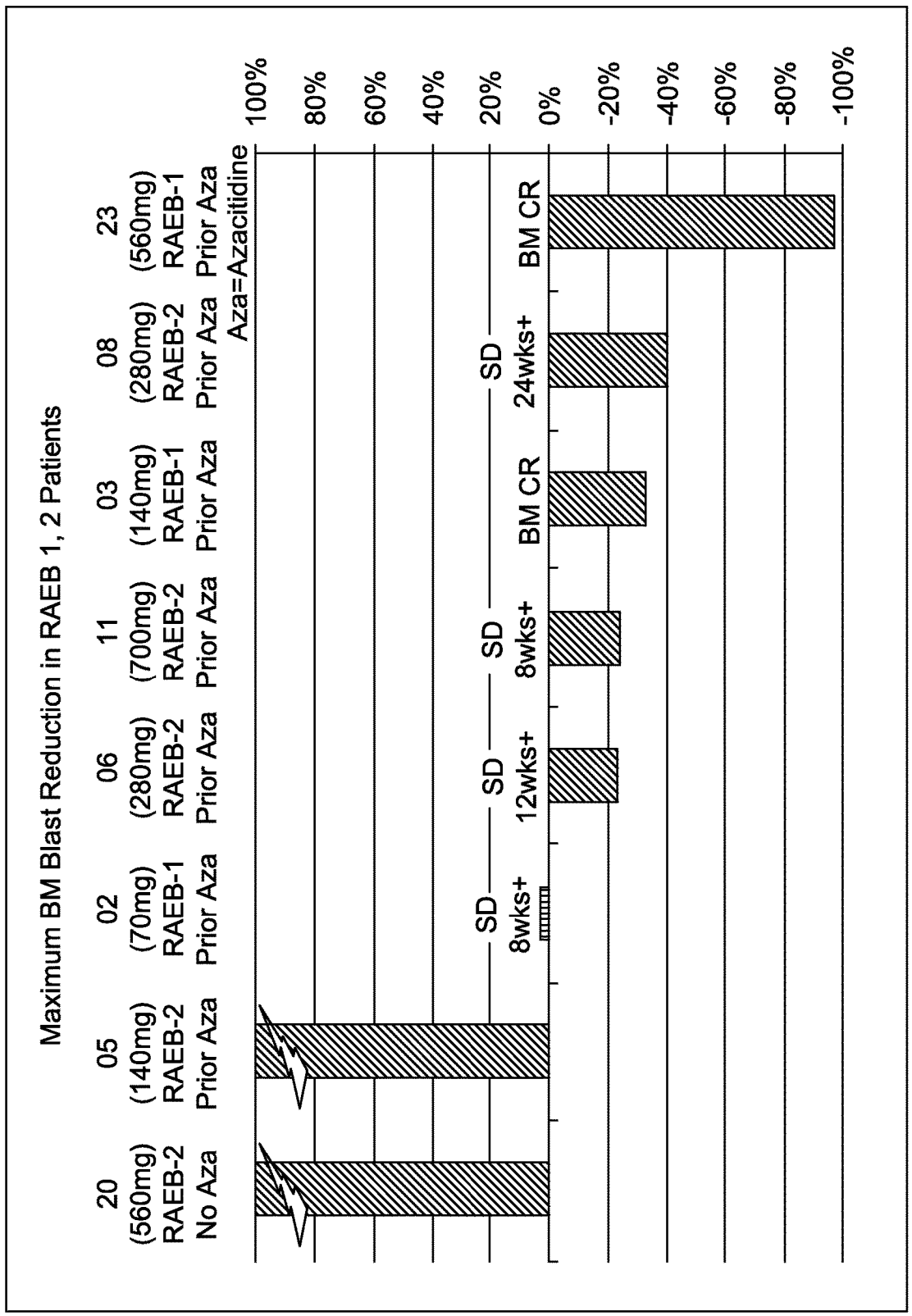

FIG. 4: This is a waterfall plot of 8 patients broken down by French American British classification (FAB) as either Refractory Anemia with Excess Blasts-1 (RAEB-1) or RAEB-2. Patients in the RAEB-2 class had a greater percentage of bone marrow and/or peripheral blood blast cells than RAEB-1 patients. The dosage level of each patient is also provided, as well as the patient history of treatment with Azacytidine. The bone marrow blast reduction is measures as a function of FAB classification, dosage and prior treatment with hypomethylating agents. 2 RAEB-2 patients, #20 and #05 do not appear to have responded to treatment irrespective of prior treatment with Azacytidine. 6 of 8 patients responded to Rigosertib, with 4 of the 6 demonstrating stable disease (SD) for periods ranging from 8 to 24 weeks. 2 Patients, #3 and #23 exhibited bone marrow complete responses (BM CR) following treatment.

Figure 5:
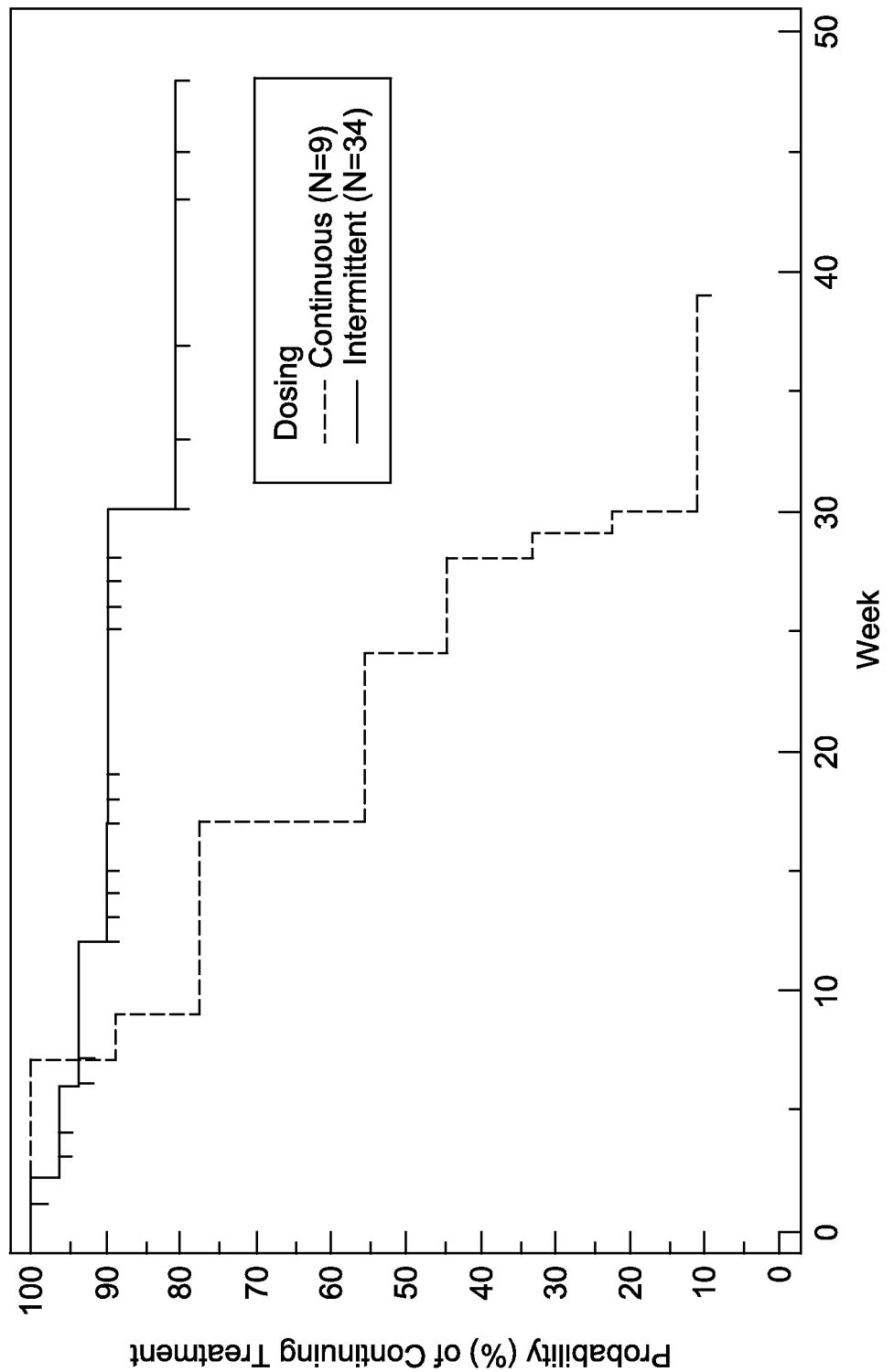

FIG. 5: Duration of treatment. Duration of treatment versus probability % of continued treatment has been measured in patients. The results show fewer treatment interruptions with intermittent vs continuous dosing. Continuous treatment employed 9 patients and median was 24 weeks. Intermittent treatment employed 34 patients and median was not reached. Study measuring the probability of a patients continuing treatment against the duration in weeks of the study. Two groups of patients were studied. One group [red line (34 patients)] received intermittent dosing of the drug. The other group [blue line (9 patients)] received continuous dosing of the drug. The results show a median duration of treatment is reached at 24 weeks for continuous treatment, whereas up to the 50 week mark, the overall percentage of patients remained very high for intermittently dosed patients, therefore a longer duration of treatment was possible with intermittent dosing.

Figure 6:
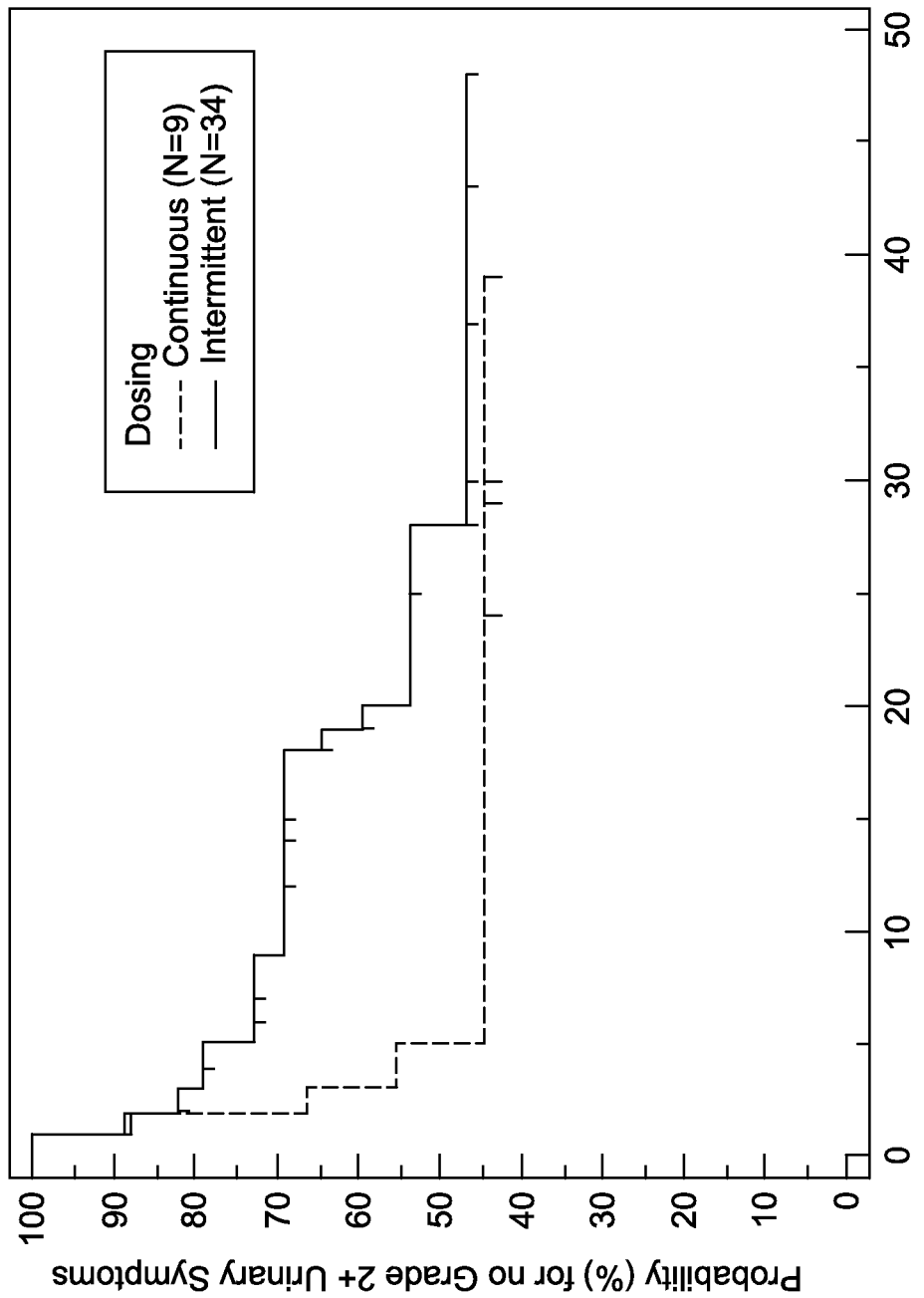

FIG. 6: Onset of grade 2+ urinary side effects. Probability (%) for no grade 2+ urinary side effects for Rigosertib intermittent versus continuous administration is demonstrated. Study measuring the likelihood of not observing grade 2+ urinary symptoms (an adverse event) as a function of time of drug exposure. Two groups of patients were studied; one group [red line (34 patients)] received intermittent dosing of the drug. The other group [blue line (9 patients)] received continuous dosing of the drug. The results showed the patients in the continuous dosing group experienced urinary symptoms at an earlier time, whereas in the intermittent dosing group, some patients did not experience symptoms until considerably later time during treatment.

Figure 7:
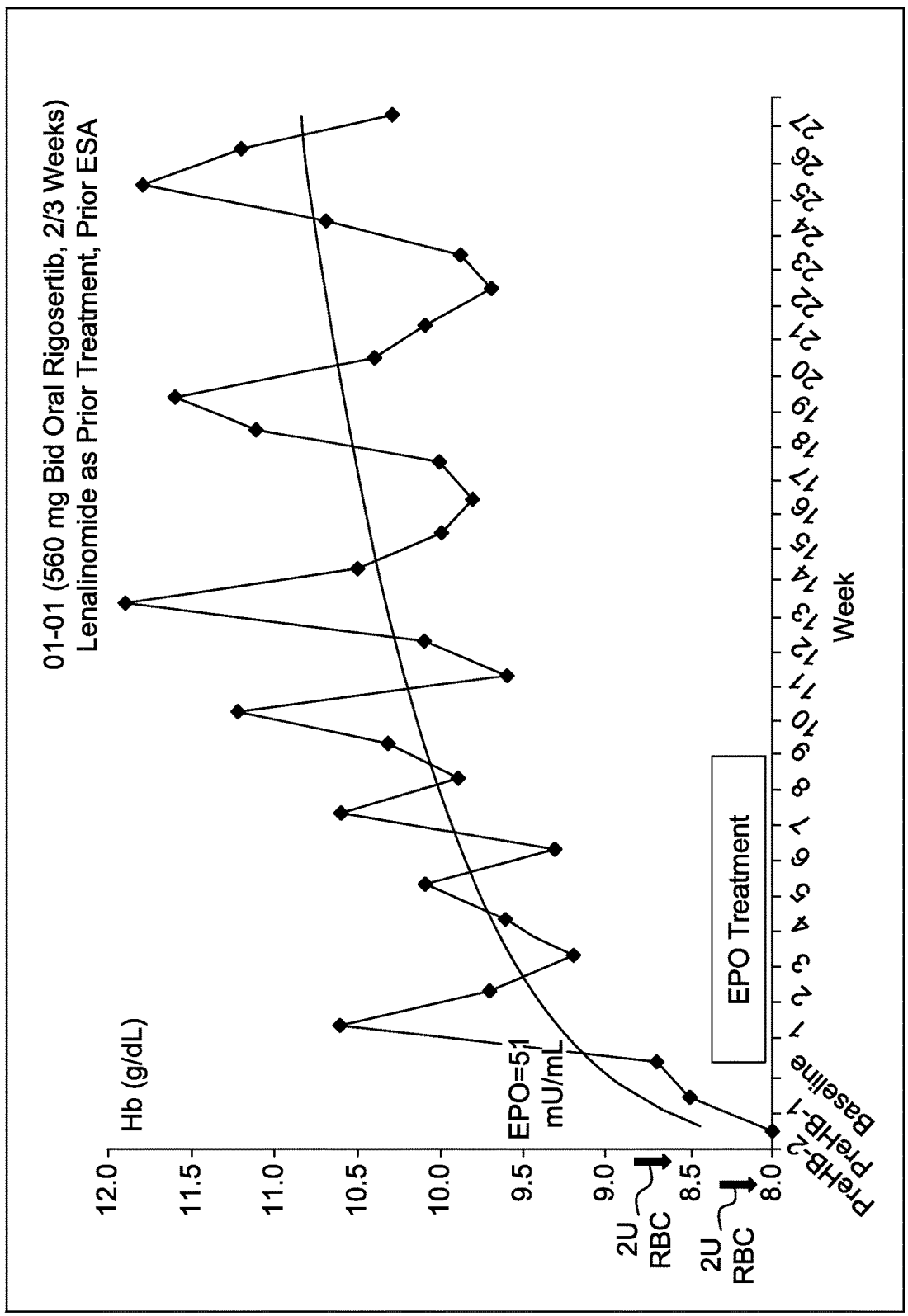

FIG. 7: Transfusion independence for 48+ weeks. Rigosertib (560 bid oral) was administered to patients in 2 or 3 weeks. Patient was administered lenalinomide and ESA as prior treatment. This graph demonstrates hemoglobin levels in a single patient, 01-01, as a function of time. The patient had received prior treatment with lenalidomide, and prior red blood cell (RBC) transfusions. On day 0, the patient received the erythroid stimulating agent (ESA) erythropoietin (EPO) to stimulate production of red blood cells. The patient then received oral Rigosertib twice per day (BID) at a dosage of 560 mg for two to three weeks. The initial spike in hemoglobin present on days one to four may be reflective of the presence of ESA, after which period the consistent rise in the level of hemoglobin measured throughout the testing period of 27 weeks is directly related to the administration of Rigosertib that helped to keep the erythroid component viable, and thus, the hemoglobin remained high during the treatment period.

Figure 8:
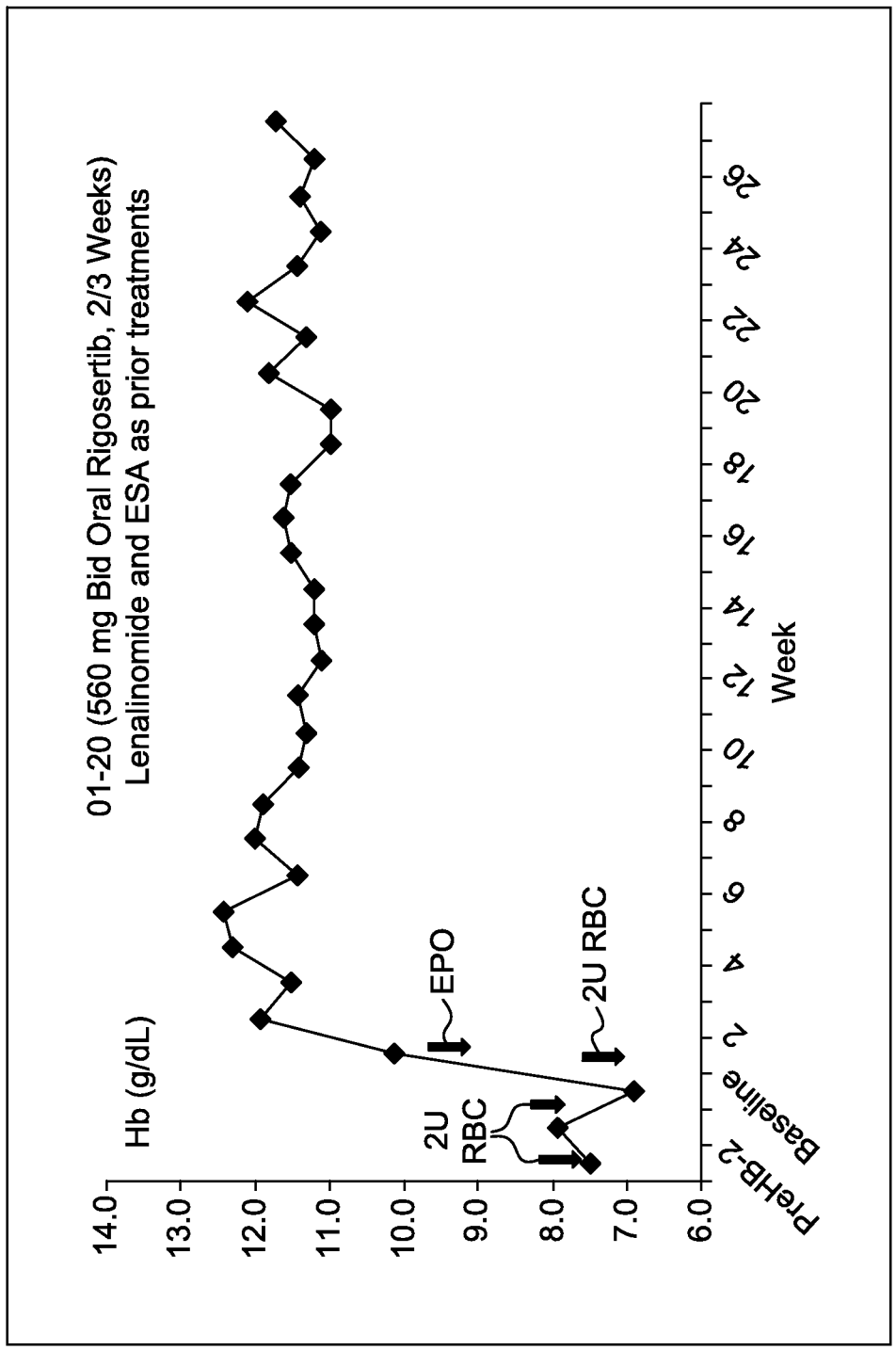

FIG. 8: Transfusion independence for 37+ weeks. Rigosertib (560 bid oral) was administered to patients in 2/3 weeks. Patient was administered lenalinomide and ESA as prior treatment. Rigosertib caused the increase in hemoglobin (Hb) and doubled platelet values from 155 platelets per µl pre-treatment to 365 platelets per µl in week 1-2. This graph demonstrates hemoglobin levels in a single patient, 01-20, as a function of time. The patient had received prior treatment with lenalidomide, and 3 prior red blood cell (RBC) transfusions. The patient received the erythroid stimulating agent (ESA) erythropoietin (EPO), to stimulate production of red blood cells. The patient then received oral Rigosertib twice per day (BID) at a dosage of 560 mg for two to three weeks. The initial spike in hemoglobin present on days one to three may be reflective of the presence of ESA, after which period the consistent rise in the level of hemoglobin measured throughout the testing period of 27 weeks is directly related to the administration of Rigosertib that helped to keep the erythroid component viable, and thus, the hemoglobin remained high, which is reinforced by the observation of a similar increase in the levels of platelets, as demonstrated in the figure.

Figure 9:
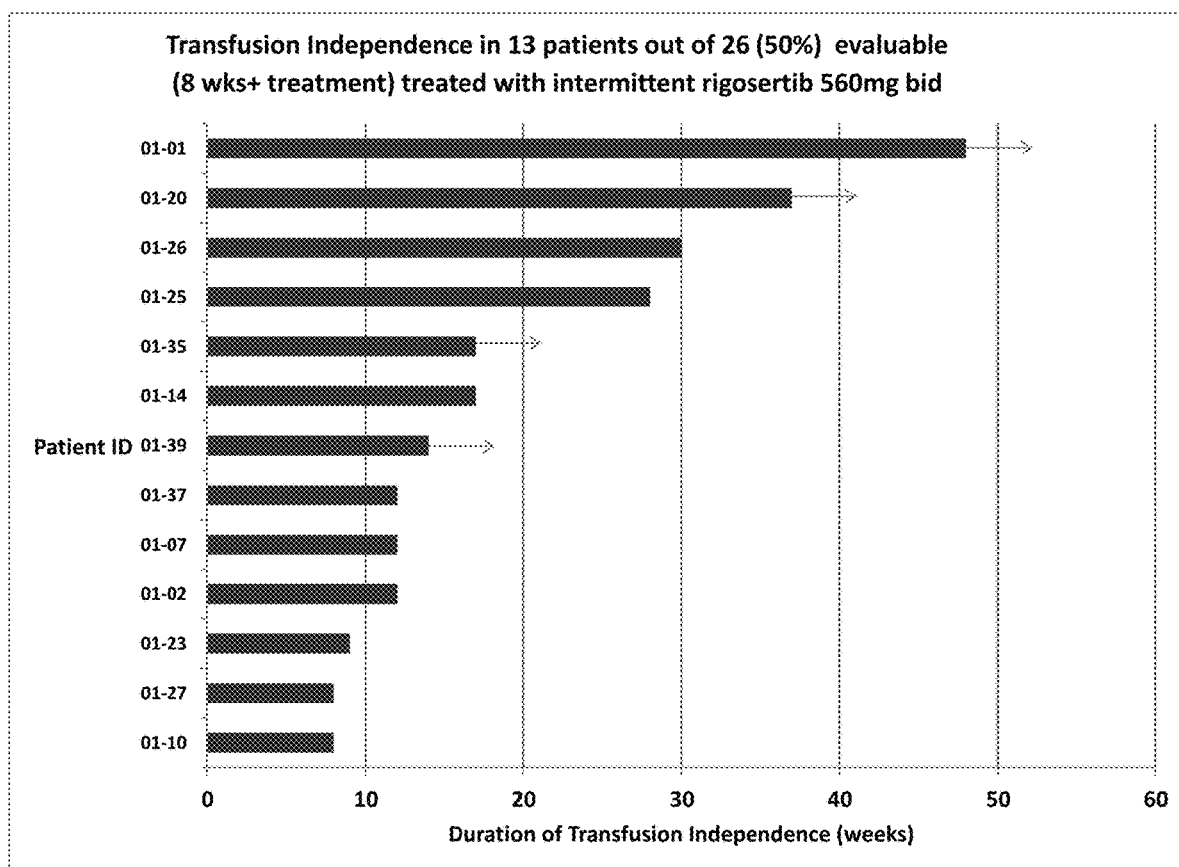

FIG. 9: Transfusion Independence in 50% of 26 Evaluable Patients. Transfusion Independence in 13 patients out of 26 (50%) evaluable, (8 wks+ treatment) treated with intermittent Rigosertib 560 mg bid. The figure shows the number of weeks of transfusion independence; arrows indicate that the transfusion benefit is still ongoing. The x axis represents weeks and the y axis represents patient identification numbers. 9 of 11 patients refractory to ESA, pre-treatment EPO levels (mU/ml)=14-361, 10 of 11 patients received concomitant ESA and 11 of the 26 evaluable patients (46%) were characterized as transfusion independent based upon no need for transfusion for 8 consecutive weeks. The graph plots each patient and the duration of transfusion independence, with a minimum of 8 weeks and a maximum of nearly 45 weeks.

Figure 10A:
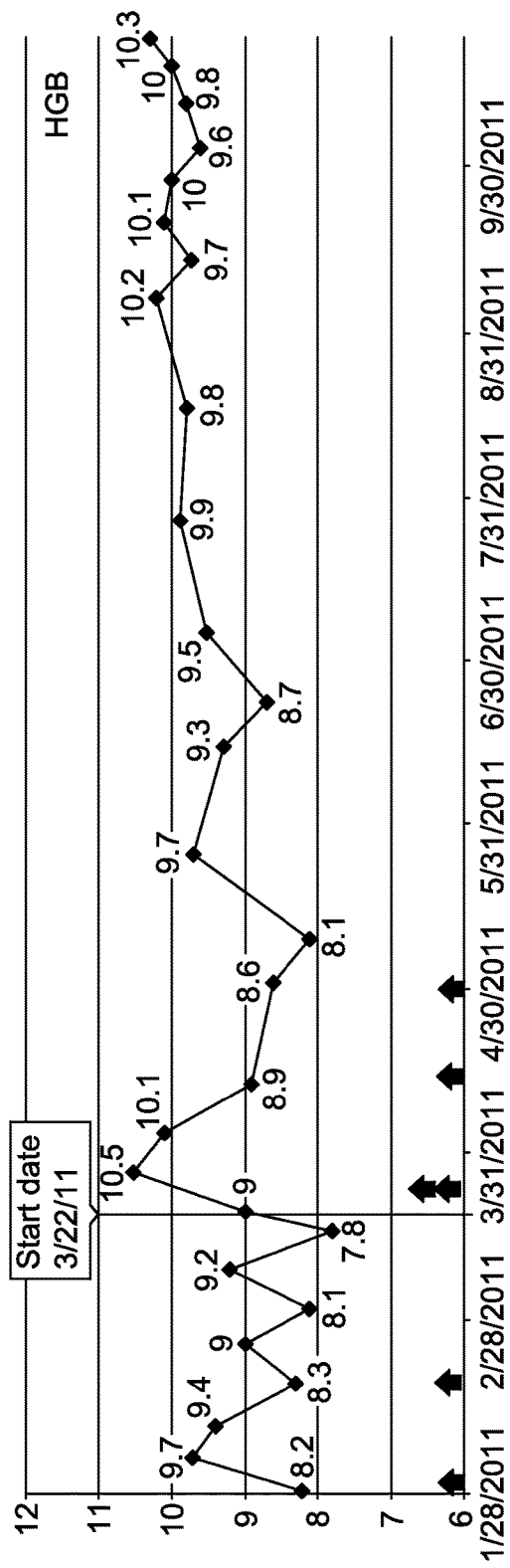
Figure 10B:
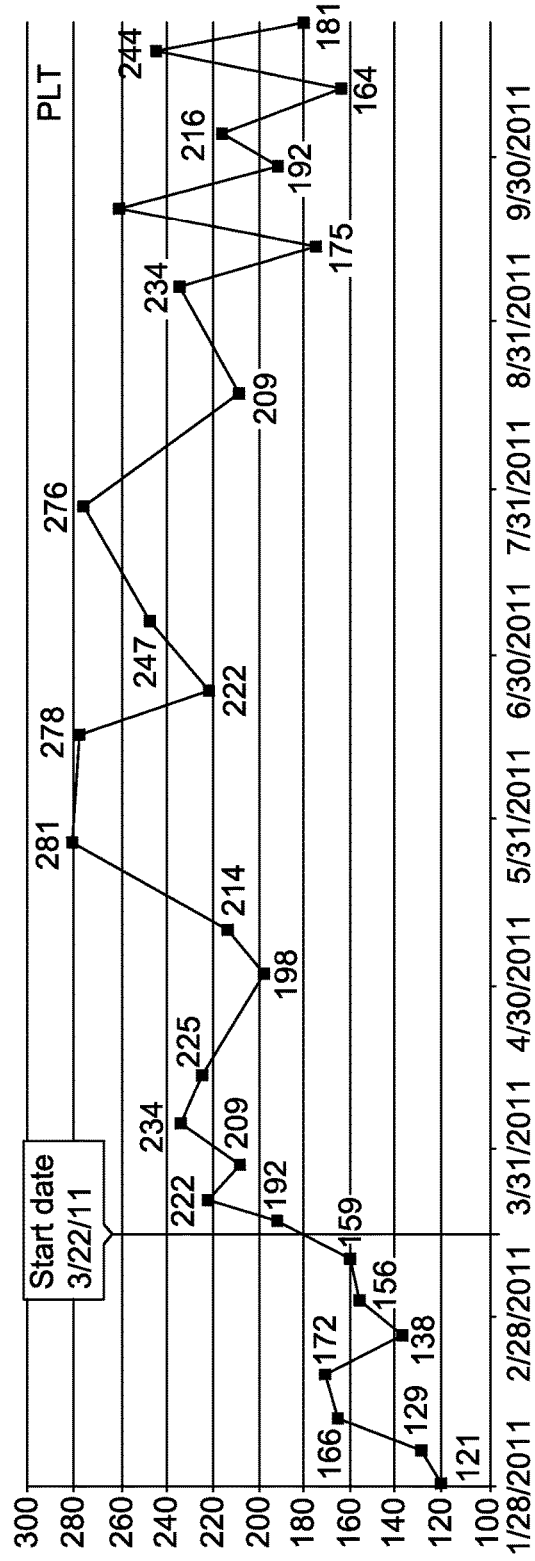

FIG. 10: Transfusion independence. Sixteen MDS Low-Int-1 Risk Transfusion Dependent Patients Treated at 560 (N=12) or 700 mg bid (N=4), 11 Males/5 Females, 54-85 ys (median=72 ys), 12 evaluable patients treated for at least 8 weeks, Transfusion dependence defined by at least 2 URBC in the prior 8 weeks. Transfusion independence (TI) defined by absence of RBC transfusion for at least 8 consecutive weeks. Erythroid Response (ER) defined by reduction of at least 4 RBC transfusions/8 weeks compared to pretreatment transfusion number in the previous 8 weeks (RBC Tx for Hb<9.0 g/dL). FIG. 10 A shows transfusion independence as shown by the level of hemoglobin (HB). FIG. 10 B shows transfusion independence as shown by the level of platelets (PLT).

Figure 11A:
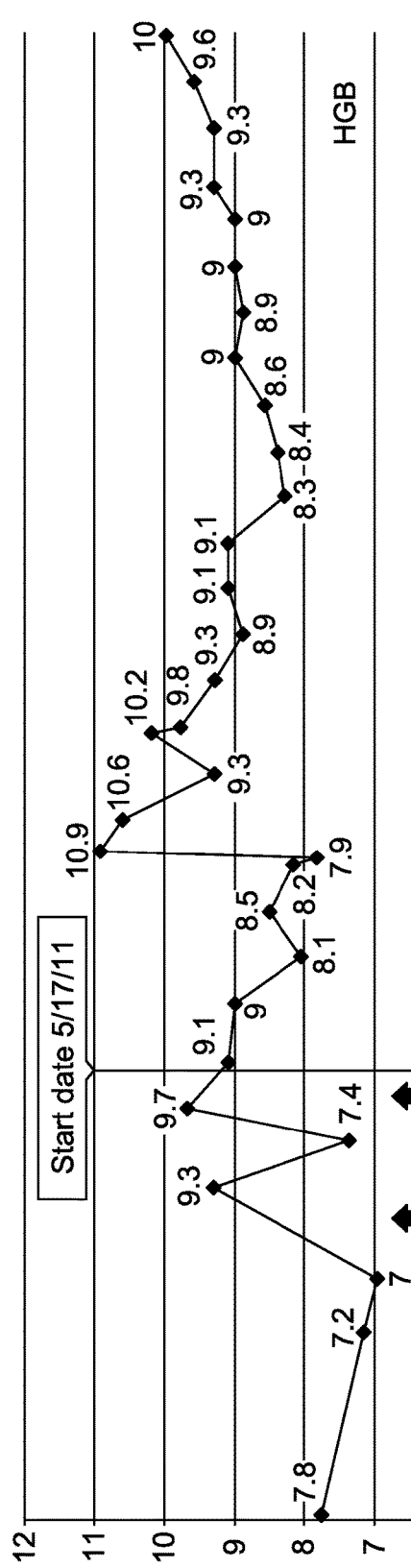
Figure 11B:
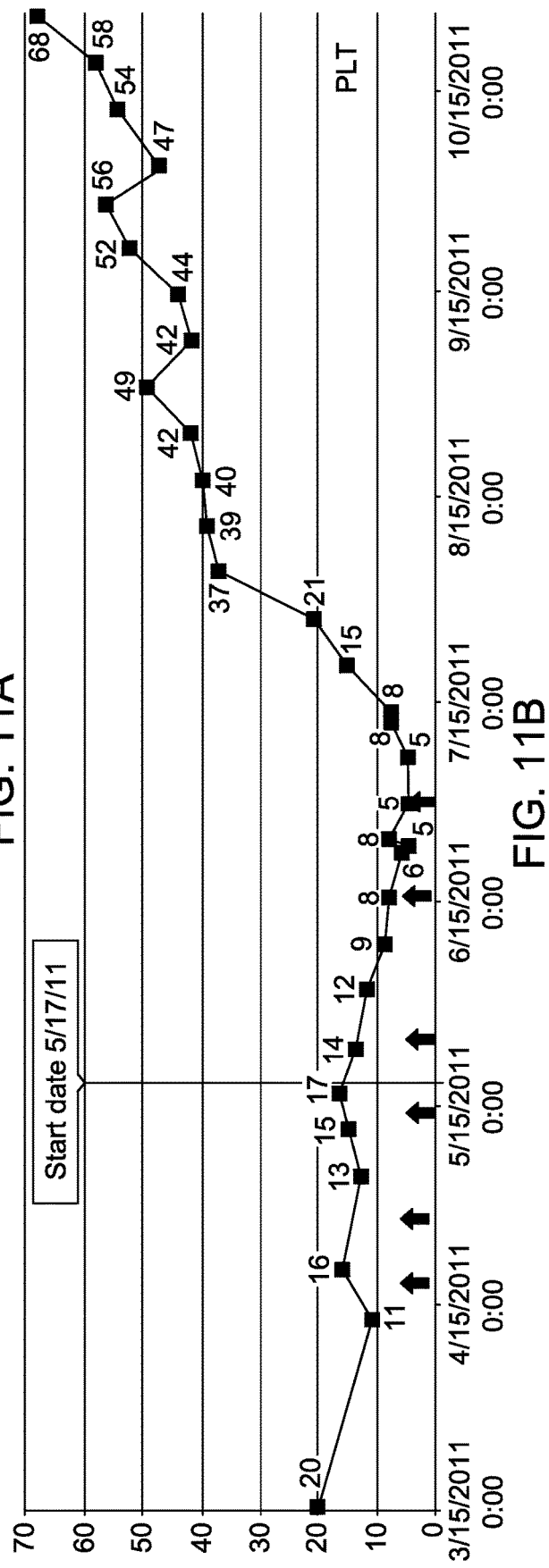

FIG. 11: Transfusion independence. FIG. 11 A shows transfusion independence as shown by the level of hemoglobin (HB). FIG. 11 B shows transfusion independence as shown by the level of platelets (PLT).

Figure 12A:
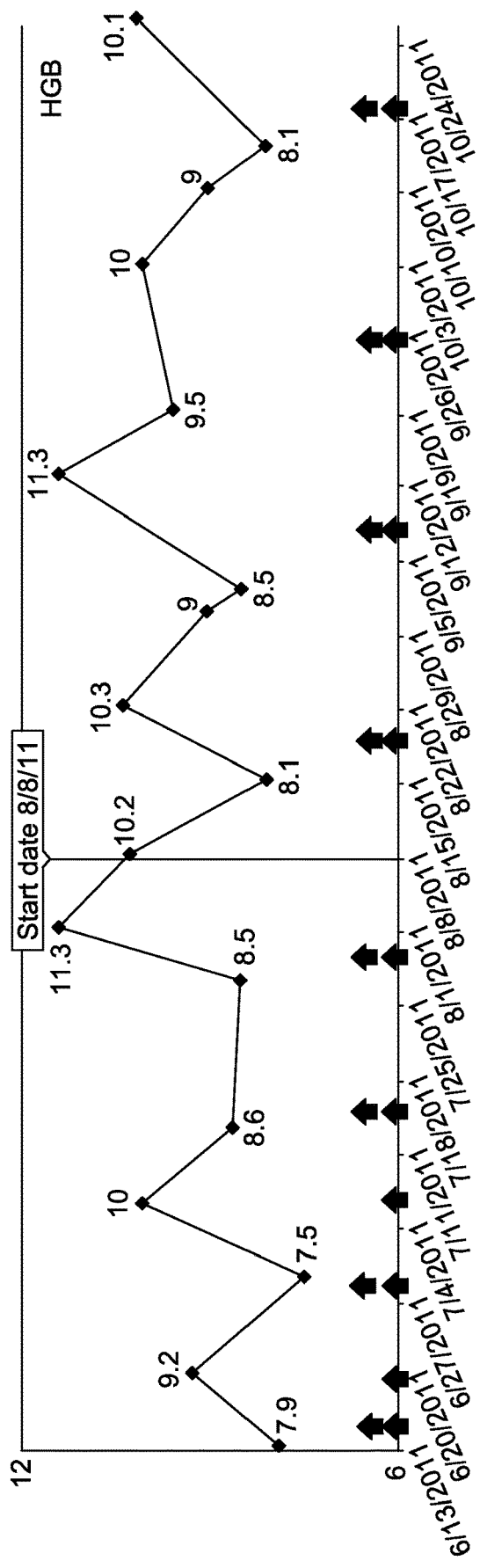
Figure 12B:
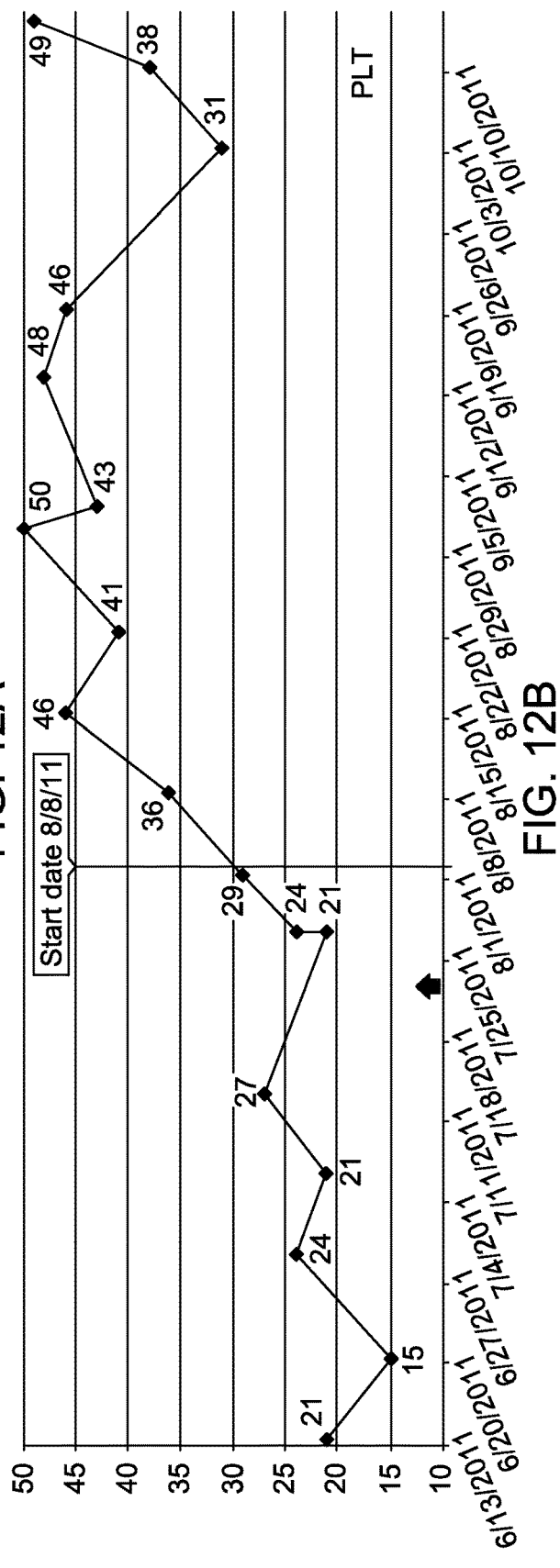

FIG. 12: Transfusion independence. FIG. 12 A shows transfusion independence with partial ER increase. FIG. 12 B shows transfusion independence with platelet increase.

Figure 13:
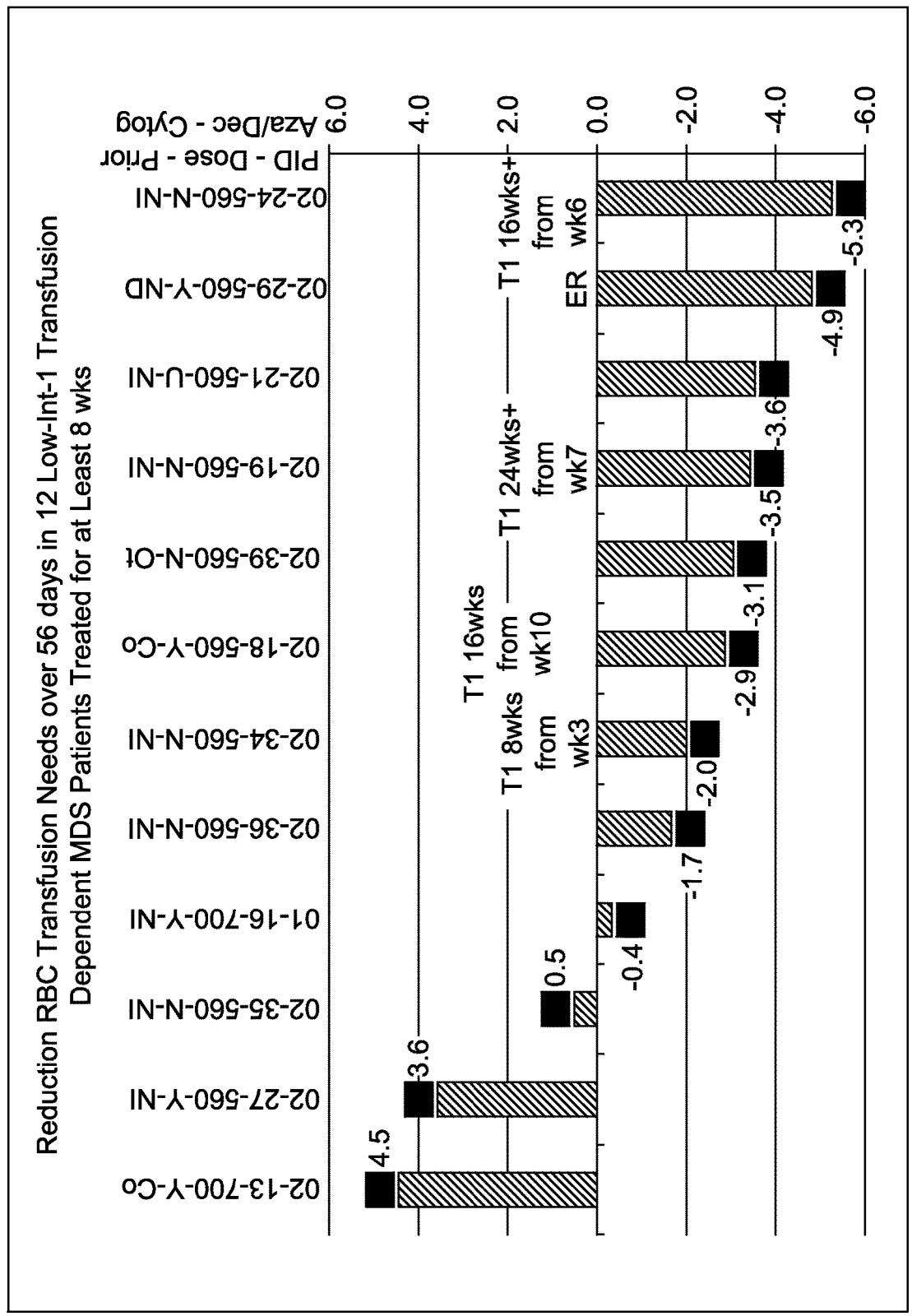

FIG. 13: Water fall plot demonstrating percentages of reduction of RBC units (absolute differences) after administration of Rigosertib versus pre-treatment needs. Each bar represents one patient. 12 individual MDS patients all categorized as low to intermediate-1 risk (International Prognostic Scoring System—IPSS) and transfusion dependent are shown. They have been treated with oral Rigosertib for 8 weeks. The decrease in transfusion requirement is plotted for each patient. The absolute differences in red blood cell (RBC) units versus pre-treatment needs are provided. The results demonstrate that 3 of 12 patients in the top panel show decrease in transfusion dependence based on RBC requirement. The administration of oral Rigosertib in lower risk transfusion dependent MDS patients resulted in a decrease of transfusion needs, expressed as a moving 8-week average variation from baseline transfusion needs.

Figure 14:
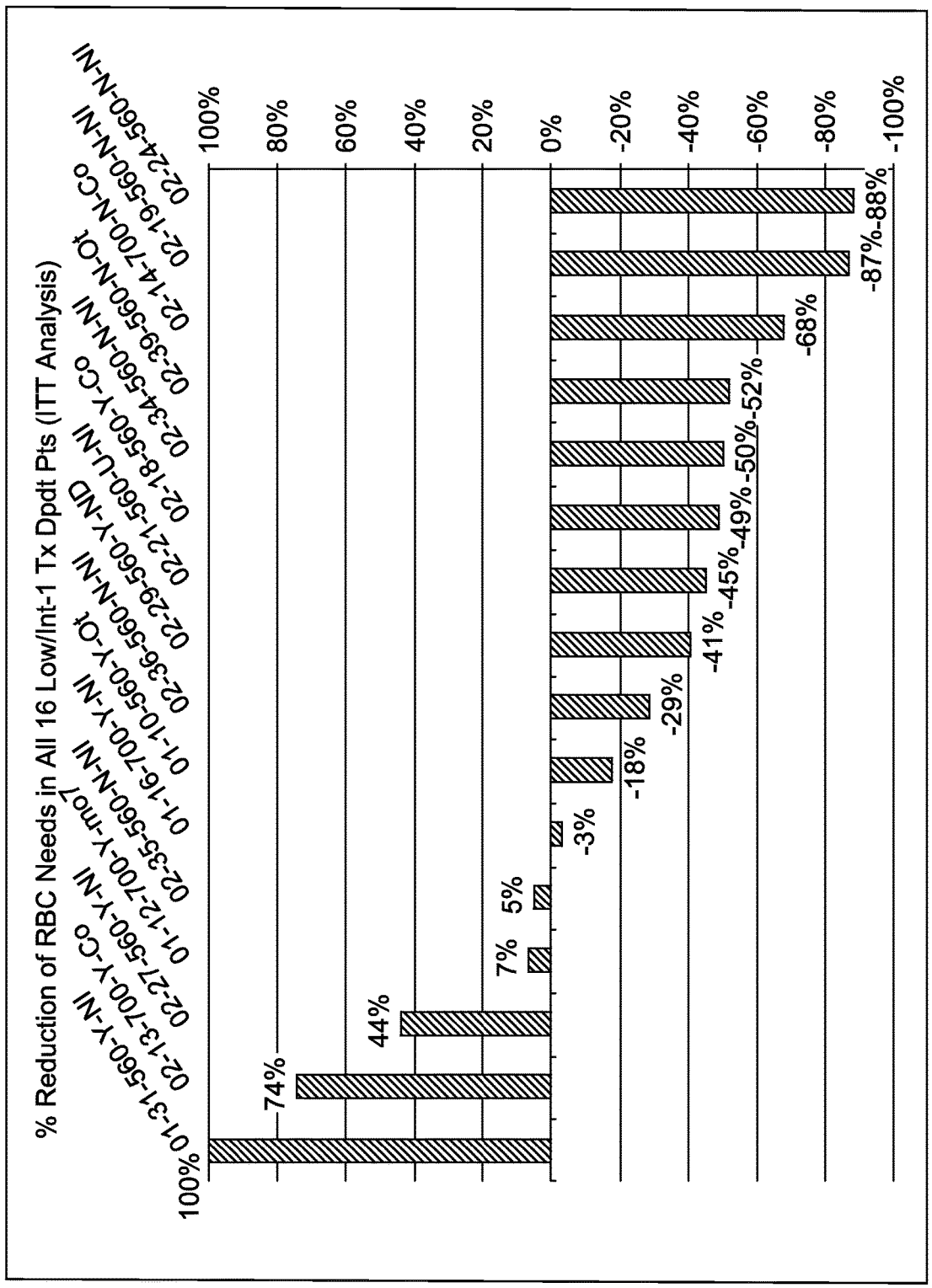

FIG. 14: Water fall plot demonstrating percentages of reduction of RBC units after administration of Rigosertib versus pre-treatment needs. A total of 16 patients are plotted against their percentage reduction in need for red blood cell transfusions after treatment versus their pre-treatment needs. 5 of 16 patients show decrease in transfusion dependence based on a decrease in percentage of RBC requirement. The administration of oral Rigosertib in lower risk transfusion dependent MDS patients resulted in a decrease of transfusion needs, expressed as a moving 8-week average variation from baseline transfusion needs.

DEFINITIONS

As used herein, "anticancer agents" are defined broadly to include agents that modulate the growth and/or metastasis of a cancer, treat or ameliorate one or more symptoms of a cancer, treat or ameliorate one or more symptoms of secondary complications of the cancer, and/or treat or ameliorate one or more symptoms of chemotherapy-induced such as chemotherapy-induced anemia (CIA).

As used herein, the terms "treat" and "treatment" are used interchangeably and are meant to indicate eradication of the disease, a postponement of development of a disorder and/or a reduction in the severity of symptoms that will or are expected to develop, which symptoms develop either as the consequence of the disease or induced by chemotherapeutic drugs. The terms further include ameliorating existing symptoms, preventing additional symptoms, and ameliorating or preventing the underlying metabolic causes of symptoms.

As used herein "effective amount" refers to the amount of a composition, or of each active agent, according to the invention that inhibits the growth of cells that are proliferating at an abnormally high rate, induces apoptosis of such cells, reduces the proportion of abnormal cells, maintaining the disease in a state of complete or partial remission, slows the progression of the disease, or the amount required to reverse drug resistance in a cancer patient, or both.

As used herein "pharmaceutical composition" refers to a composition that contains at least one compound of Formula 1 or an agonist, antagonist, biologically active fragments, variants, analogs, isomers (structural isomers and stereoisomers and racemic mixtures) modified analogs, and functional analogs of at least one compound of Formula 1. The pharmaceutical composition of the invention may also contain additional anticancer agents as defined herein.

As used herein "about" refers to a range of 15% lower or higher than the actual numerical value recited.

IV. DETAILED DESCRIPTION OF THE INVENTION

The invention as disclosed and described herein provides novel compositions and methods for treatment of cancer. The composition of the invention includes at least one compound according to Formula 1:

Formula 1

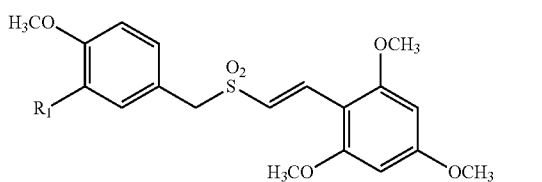

Where $R_1$ is selected from the group consisting of —$NH_2$, —NH—$CH_2$—COOH, —NH—CH($CH_3$)—COOH, —NH—C($CH_3$)$_2$—COOH, —NH—$CH_2$—$CH_2$—OH and —N—($CH_2CH_2OH$)$_2$ or a pharmaceutically acceptable salt of such a compound, and an anticancer agent.

A comprehensive list of compounds presented by Formula 1 according to this invention is disclosed in U.S. Pat. Nos. 8,063,109 and 8,476,320 issued to Stanley Bell and Manoj Maniar, the entire contents of each of which are specifically incorporated herein by reference.

The pharmaceutical composition of the invention may also additionally contain one or more anticancer agents, which are chemically attached to a compound of Formula 1 or administered as separate chemical entities.

A preferred compound of the invention is Rigosertib (Formula 1 A)

Formula 1A

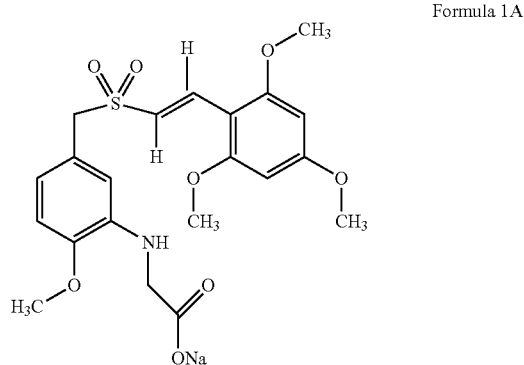

According to one embodiment of the invention, the compound of the invention can be administered to drug resistant cancer patients, prior to, concomitant with, and/or subsequent to the administration of the specific anticancer agent to which the cancer patient has acquired resistance.

Examples of anticancer agents include, cytotoxic agents, chemotherapeutic agents (including alkylating agents, antimetabolites, anthracyclines, alkaloids, topoisomerase inhibitors, monoclonal antibodies, among others), erythropoiesis modulating agents comprising ESAs including EPO (endogenous, recombinant and/or synthetic EPO), epoetin alfa, Procrit, Epogen, epoetin beta, darbepoetin alfa, and/or methoxy polyethylene glycol-epoetin beta; DNA methyltransferase inhibitors (including azacitidine, decitabine, 5-fluoro-2'-deoxycitidine, 5,6-dihydro-5-azacytidine, zebularine, fazarabine, hydralizine, procaine, procainamide, epigallocatechin gallate, psammaplin A, or (S)-2-(1,3-fioxo-1,3-dihydro-isoindol-2-yl)-3-(1H-indol-3-yl)-propionic acid, or a pharmaceutically acceptable salt thereof), immunomodulators such as lenalidomide, among others.

Failure of a patient's cancer to respond to a specific therapy can result from one of two general causes: host factors and specific genetic or epigenetic alterations in the cancer cells. Host factors include poor absorption or rapid metabolism or excretion of a drug, resulting in low serum levels; poor tolerance to effects of a drug, especially in elderly patients, resulting in a need to reduce doses below optimal levels; inability to deliver a drug to the site of a tumor, as could occur with bulky tumors or with biological agents of high molecular weight and low tissue penetration such as monoclonal antibodies and immunotoxins. In addition, various alterations in the host-tumor environment can affect the response of the tumor to cancer therapy, these effects include local metabolism of a drug by normal cells, abnormal and/or unusual features of the tumor blood supply that may affect transit time of drugs within tumors, among others.

The pharmaceutical composition of the invention and the therapeutic regimen as claimed are effective to overcome one or more of the aforementioned obstacles in cancer therapy by raising the tolerance or resistance to anticancer agents or therapies. Accordingly, the method of the invention provides additional tools for effective cancer therapy to combat and defeat drug resistance in cancer patients.

Multidrug resistance, the principal mechanism by which many cancers develop resistance to chemotherapy drugs, is a major factor in the failure of many forms of chemotherapy. It affects patients with a variety of blood cancers and solid tumors. Tumors usually consist of mixed populations of malignant cells, some of which are drug-sensitive while others are drug-resistant. Chemotherapy can destroy drug-sensitive cells, but leaves behind a higher proportion of drug-resistant cells. As the tumor begins to grow again, chemotherapy may fail because the remaining tumor cells are now drug resistant.

Resistance to therapy has been correlated to the presence of at least two molecular "pumps" in tumor-cell membranes that actively expel chemotherapy drugs from the interior. This allows tumor cells to avoid the toxic effects of the drug or molecular processes within the nucleus or the cytoplasm. The two pumps commonly found to confer chemo-resistance in cancer are P-glycoprotein and the so-called multidrug resistance-associated protein (MRP). Because of their function and importance, they are the targets of several anticancer efforts.

According to one embodiment, the compositions and methods of the invention overcome resistance to DNA methyltransferase inhibitors, ESAs, or a combination thereof.

The methods and compositions of the invention are useful in treatment of cancer and the anemia associated with cancer, specifically in patients who have acquired resistance to exogenous erythropoietin (EPO). Resistance to exogenous EPO is associated with an increased risk of death. Anemia in cancer patients rises through many different mechanism of actions and pathways, it can be the direct effects of the cancer cells in the body, as a result of biologically active products of the cancer cells, or as a consequence of the treatment of cancer. There is also an association between anemia and progression of blood cancers. The main causes of anemia are deficient production of erythropoietin (EPO), iron deficiency, and a chronic disease with endogenous EPO resistance. Up to 10% of patients receiving EPO are hyporesponsive to therapy and require large doses of the agent. Proinflammatory cytokines antagonize the action of EPO by exerting an inhibitory effect on erythroid progenitor cells and by disrupting iron metabolism.

The compounds of the invention possess a non-ATP competitive multi-kinase inhibitor activity with the ability to differentially arrests tumor cells in G2-M stages and inhibits polo-like kinase and PI-3 kinase pathways. The compounds of the invention also have the ability to decrease Cyclin-D1 and Akt phosphorylation. According to one embodiment of the invention, the biological activity of the pharmaceutical compositions and methods of the invention includes induction of apoptosis in proliferative cells and tissues.

Malignant and metastatic conditions which can be treated with the therapeutic method of the invention include, but are not limited to, hematological cancers and solid tumors, including all cancers described herein and otherwise known in the art (for a review of such disorders, see Fishman et al., Medicine, 2d Ed., J. B. Lippincott Co., Philadelphia (1985)).

Hematological malignancies are the type of cancers that affect blood, bone marrow, and lymph nodes. As the three lineages are intimately connected through the immune system, a disease affecting one of the three lineages will often affect the other lineages. For example, although lymphoma is a disease of the lymph nodes, it often spreads to the bone marrow, affecting the blood and occasionally producing a paraprotein.

Hematological cancers usually derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin. Examples of hematological diseases include, but are not limited to, Leukemias, acute lymphoblastic leukemia (ALL), acute myelogenous leukemia (AML), MDS (Myelodysplastic Syndrome), MPN (Myeloproliferative neoplasm), MDS/MPN overlap, and PDGFR/FGFR1-rearranged myeloid/lymphoid neoplasms with eosinophilia, chronic lymphocytic leukemia (CLL), small lymphocytic lymphoma (SLL), chronic myelogenous leukemia (CML), acute monocytic leukemia (AMOL), lymphomas, Hodgkin's lymphomas (all four subtypes), and non-Hodgkin's lymphomas, among others.

Examples of solid tumors include cancer of prostate, lung, breast, ovarian, stomach, pancreas, larynx, esophagus, testes, liver, parotid, biliary tract, colon, rectum, cervix, uterus, endometrium, kidney, bladder, thyroid cancer; primary tumors and metastases, melanomas; glioblastoma, Kaposi's sarcoma; leiomyosarcoma, non-small cell lung cancer, and colorectal cancer, among others.

The pharmaceutical compositions and methods of the invention are particularly effective in treating and/or ameliorating symptoms of diseases related to hematopoietic stem cells. The cellular elements of blood originate from the pluripotent hematopoietic stem cell. Stem cells have extensive regenerative and differentiating capacity and generate lymphoid and myeloid precursors, which then produce lymphocytes, neutrophils, eosinophils, basophils, erythrocytes, and platelets. In myelodysplastic syndrome, a dysregulation in the differentiation process appears to occur. Mortality in myelodysplastic syndrome is related to bleeding, recurrent infection, and leukemic transformation. In the absence of treatment, myelodysplastic syndrome can be a rapidly fatal disease, with or without the transformation to acute myeloid leukemia. An estimated 20-40% of adults with myelodysplastic syndrome develop leukemia, and 30-40% of myelodysplastic syndrome patients succumb to infection, bleeding, or both.

A prognostic scoring system, the International Prognostic Scoring System (IPSS), has been developed for patients with myelodysplastic syndrome. The IPSS is a consensus prognostic scoring system based on cytogenetic, morphological, and clinical data from seven large risk-based studies that had each generated prognostic systems. P. Greenberg, et al, "International Scoring System for Evaluating Prognosis in Myelodysplastic Syndromes", Blood, 1997, 89(6) 2079-88. Compared with prior risk-based classifications, the IPSS provides an improved method for evaluating prognosis in MDS. Based on univariate analysis it was found that the major variables having an impact on disease outcome for evolution to acute myeloid leukemia were cytogenetic abnormalities, the percentage of bone marrow myeloblasts, and the number of cytopenias. Factors for survival, in addition to the above variables, also included age and gender.

The cytogenetic subgroups of outcome were classified as follows: "Good" outcomes were normal, Y alone, del(5q) alone, del(20q) alone; "Poor" outcomes were complex (i.e. delta.3 abnormalities) or chromosome 7 anomalies; "Intermediate" outcomes were other abnormalities.

Multivariate analysis combined these cytogenetic subgroups with the percentage of bone marrow blasts and the number of cytopenias to generate a prognostic model. Weighting these variables by their statistical power separated patients into distinctive subgroups of risk for 25% evolution to acute myeloid leukemia: low, 9.4 years; intermediate-1 (INT-1), 3.3 years; intermediate-2 (INT-2), 1.1 years; and high, 0.2 year. These same features also separated patients into similar distinctive risk groups for median survival: low, 5.7 years; INT-1, 3.5 years; INT-2, 1.2 years; and high, 0.4 year.

Acute myeloid leukemia is the most common variant of acute leukemia occurring in adults, comprising approximately 80-85% of cases of acute leukemia diagnosed in individuals greater than 20 years of age. The heterogeneous group of acute leukemic disorders of myeloid hematopoietic cells has been called a variety of names including acute myelogenous leukemia, acute myelocytic leukemia, acute myeloid leukemia, acute myeloblastic leukemia, acute granulocytic leukemia, and acute nonlymphocytic leukemia. The myeloid character of the reddynant blasts can be determined by detection of characteristic morphologic and immunologic findings. Clinical aspects of the disease are reviewed by C. A. Schiffer and R. M. Stone in Cancer Medicine, Ed. David W. Kufe et al., 6.sup.th Edition, B. C. Decker, 2003, the entire disclosure of which is incorporated herein by reference.

The pharmaceutical composition of the invention includes specific compounds of styryl benzyl sulfones that have exhibited selective chemotherapeutic activities towards cancer cells. Most cancer drugs destroy cancer cells by disrupting the cell division machinery, which makes them also poisonous to normal cells and thus induce serious side effects. An extensive body of work undertaken by Reddy et al on design, synthesis and biological activity of kinase inhibitors resulted in identification of compounds of styryl benzyl sulfones as multi-kinase inhibitors (see, for example, U.S. Pat. Nos. 6,201,154; 6,359,013; 6,414,034; 6,486,210; 6,541,475; 6,548,553; 6,576,675; 6,599,932; 6,787,667; 6,833,480; 7,053,123; 7,056,953 and 7,598,232), the contents of each of the aforementioned patents are specifically incorporated herein by reference.

Most kinase inhibitors that have been developed over the years act through displacing the molecule of ATP from its binding pocket. Mutations in the ATP-binding pocket disrupt binding of the inhibitor to the ATP-binding pocket and as a consequence the kinase inhibitors will cease action overtime as the subject under treatment develops resistance to the drug. An important pathway that is crucial to cell division is the one involving Polo-like kinase or Plk1. Plk1 is active in cells that are in the process of dividing, therefore, majority of cells in the body that are in the $G_0$ resting phase do not contain Plk-1. In contrast, most cancer cells express high levels of Plk-1. When Plk-1 function is blocked in cancer cells, chromosomes become disorganized, centrosomes become abnormal and the cells lose their ability to divide properly and apoptosis occurs.

Rigosertib is a small molecule targeted as an anti-cancer agent designed to inhibit critical pathways involved in the growth and survival of cancer cells. This drug is a non-ATP competitive multi-kinase inhibitor which differentially arrests tumor cells in G2-M stages and inhibits polo-like kinase and PI-3 kinase pathways with decreases of Cyclin-D1 and Akt phosphorylation. The dual molecular mechanism of action of Rigosertib (targeting the PI-3 kinases and the PLK mitotic pathway) results in the induction of multiple centrosomes during cell division, resulting in a multipolar spindle and total disorganization of the mitotic apparatus leading to chromosomal catastrophe; modulation of the ERK/MAPK (growth) and AKT (survival) pathways, promoting cell death (apoptosis) in cancer cells.

Due to the dual effect on tumor cell survival and mitotic pathways, Rigosertib has potential utility in a variety of cancer types, including hematological malignancies and solid tumors. Ongoing clinical trials are evaluating the activity of Rigosertib in MDS: Phase III and Phase II trials, other blood malignancies including AML and CLL: Phase I trials, solid tumors, including randomized Phase II in metastatic pancreatic cancer and Phase II in ovarian cancer.

In general, the compositions may be administered by the transdermal, intraperitoneal, intracranial, intracerebroventricular, intracerebral, intravaginal, intrauterine, oral, rectal, ophthalmic (including intravitreal or intracameral), nasal, topical (including buccal and sublingual), parenteral (including subcutaneous, intraperitoneal, intramuscular, intravenous, intradermal, intracranial, intratracheal, and epidural) administration.

Oral formulation can include standard carriers such as pharmaceutical grades of mannitol, lactose, starch, magnesium stearate, sodium saccharine, cellulose, magnesium carbonate, etc. Such compositions contain a therapeutically effective amount of the compound, preferably in purified form, together with a suitable amount of carrier so as to provide the form for proper administration to the patient. The formulation should suit the mode of administration.

In a preferred embodiment, the composition of the invention is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition of the invention is to be administered by infusion, it can be dispensed with an infusion bottle containing sterile pharmaceutical grade water or saline. Where the composition of the invention is administered by injection, an ampoule of sterile water for injection or saline can be provided so that the ingredients may be mixed prior to administration.

In addition, the compounds and compositions of the invention may be incorporated into biodegradable polymers allowing for sustained release of the compound, the polymers being implanted in the vicinity of where drug delivery is desired, for example, at the site of a tumor or implanted so that the composition is slowly released systemically. Osmotic mini-pumps may also be used to provide controlled delivery of high concentrations of the composition of cancer markers through cannulae to the site of interest, such as directly into a metastatic growth or into the vascular supply to that tumor.

The pharmaceutical compositions of the invention have been presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

The pharmaceutical compositions of the invention may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

In a preferred embodiment, Rigosertib (ON 01019.Na) has been used in an ongoing and completed Phase I, Phase II and Phase III clinical trials and has generated data in over 680 patients with advanced, heavily pre-treated cancer and have demonstrated a desirable safety profile for Rigosertib. A low frequency of Grade 3 and 4 toxicities (that are commonly associated with standard chemotherapy and other kinase inhibitors) have been observed with Rigosertib treatment.

Rigosertib can be taken either orally or via intravenous infusion, once circulating in the blood stream it is distributed throughout the body, crosses the cell membrane and enters the nucleus of cells where it binds to its target. Rigosertib inhibits PLK1 pathway preventing PLK1 roles in the cell-cycle and cell division which leads to cell arrest and programmed cell death in cancer cells. This specificity for cancer cells improves the efficacy of the drug and minimizes the drug related toxicity. Gumireddy et al (Cancer Cell 2005, 7, 275-286), incorporated herein by reference, identified sodium (E)-2-{2-methoxy-5-[(2',4',6'-trimethoxystyrylsulfonyl) methyl]phenyl amino}acetate, ON 01910.Na, (Rigosertib) as a potent anticancer agent and a non-ATP-competitive small molecule inhibitor of Plk1 pathway.

Further evaluations by Reddy et al (J Med Chem, 2008, 51, 86-100 and J Med Chem 2011, 54, 6254-6276; and U.S. Pat. No. 7,598,232) resulted in identification of several potent multi-kinase inhibitors. ON 01910.Na (Rigosertib), while non-toxic to normal cells, selectively induces mitotic arrest leading to apoptosis in cancer cells and myeloblasts. What is unique about Rigosertib and the many other kinase inhibitors that Reddy's team has developed is that they block kinase activity in a way that does not involve the ATP-binding pocket and therefore drug resistance has not been a problem. In fact, resistance to Rigosertib was not detected for several years when cells were grown in presence of the inhibitor.

Biological activity of the intravenous formulation of Rigosertib has been demonstrated in MDS patients who failed prior treatment with hypomethylating agents (American Society of Hematology Annual Meeting, San Diego, Calif., December 2011). The novel oral formulations of Rigosertib described herein is highly bioavailable under fasting condition and shows significant advantage over the IV formulation.

Earlier clinical studies in advanced solid tumors as well as in MDS and acute leukemia reported a favorable toxicity profile and showed early evidence of clinical activity for Rigosertib.

Extensive Phase I, Phase II and Phase III studies with Rigosertib have been or are being conducted at leading institutions in the U.S. and abroad in more than 600 patients with solid tumors and hematological cancers, including MDS and AML. MDS and AML are blood disorders widely recognized as difficult to manage, with limited therapeutic options available for patients, especially those with drug-resistant disease.

Rigosertib has been safe and active in MDS and AML patients treated in Phase I and Phase II clinical trials designed to determine the optimal dose and anti-leukemia efficacy of this drug. These studies are a part of comprehensive evaluation of the safety and activity of Rigosertib. To date, more than 70 patients with MDS or AML have been treated in phase I and Phase II trials. These studies have led to an ongoing multi-site Phase III pivotal trial in higher risk MDS patients who have failed prior treatment with hypomethylating agents, under a Special Protocol Assessment (SPA) from the U.S. FDA.

According to one embodiment, Rigosertib was given as an intravenous infusion to MDS patients. In one trial, patients received 800 mg Rigosertib for three to five days every other week. According to another embodiment, patients received 650 to 1,700 mg Rigosertib for three to six days every other week. According to yet another embodiment, patients were initially treated with 800 mg to 1,500 mg Rigosertib for two days every week for three weeks followed by one week without treatment. The treatment schedule in these studies was later changed to 1,800 mg Rigosertib for three days every other week. In general, patients showed at least a 50 percent decrease or stabilization in the number of immature bone marrow cells (blasts).

It is intended herein that by recitation of such specified ranges the ranges recited also include all those specific integer amounts between the recited ranges. For example, the range of about 650 mg to 1,700 mg Rigosertib or 800 mg to 1,500 mg Rigosertib, it is intended to also encompass 600 mg, 750 mg, 850 mg, 900 mg, 950 mg, 1000 mg, 1100 mg, 1200 mg, 1300 mg, 1400 mg, 1600 mg, and 1800 mg Rigosertib.

In another embodiment, the efficacy of Rigosertib was shown in higher risk MDS patients who had previously failed treatment with Vidaza (azacitidine) or Dacogen (decitabine). They found that previous treatment failure did not have a negative impact on response to Rigosertib. These patients experienced at least a 50 percent decrease or stabilization in the number of immature bone marrow cells, and their median survival was about 36 weeks.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

V. EXAMPLES

Example 1

Preparation of 280 mg Oral ON 01910.Na (Rigosertib) Soft Gelatin Capsules

Soft gelatin capsules of Rigosertib were composed of ON 01910.Na yellow colored oblong shaped opaque capsules containing a thick clear solution. These capsules additionally contained Gelatin, NF; Glycerin, USP; Sorbitol Sorbitan Solution, NF; Opatint White (G-18000); FD&C Yellow #6 powder; D&C Yellow #10; and Purified Water, USP. Rigosertib capsules were manufactured in 280 mg strength as follows. Each 280 mg strength capsule weighing 1000 mg contained 280 mg ON 01910.Na dissolved in 673.4 mg Polyethylene Glycol 400, NF, (Dow Chemical Company); 20 mg Polyethylene Glycol 4000, NF, (Dow Chemical Company) and 26.6 mg purified water, USP.

The manufacturing process for the 280 mg drug product involved adding ON 01910.Na to PEG 400, in a stainless steel container under a nitrogen blanket. The product was homogenized at 15° C. to 20° C. until the excipients and the drug were completely dispersed. The product was held at room temperature for 9 to 12 hours and then was checked visually for any un-dissolved particles. If un-dissolved particles were present, the contents were homogenized in an ice bath or chiller for 30 to 60 minutes. The contents were then passed through a #40 mesh hand screen and then all screened material was collected. The product was vacuum deaerated for not less than an hour and until no air bubbles were observed. The product was then encapsulated, dried and inspected visually to remove leakers, odds, under fills, and stickiness.

Example 2

Preparation of 70 mg Oral ON 01910.Na (Rigosertib) Soft Gelatin Capsules

Rigosertib clear transparent oblong shaped soft gelatin capsules containing a clear solution were manufactured in 70 mg strength capsule as in Example 1. Each 70 mg strength capsule weighing 1000 mg contained 70 mg ON 01910.Na dissolved in 930 mg Polyethylene Glycol 400, NF (Dow Chemical Company). The manufacturing process for the 70 mg drug product involved adding ON 01910.Na bulk to PEG 400 in a stainless steel container under a nitrogen blanket. The product was then homogenized at 15° C. to 20° C. until the ON 01910.Na was completely dissolved. The mixture was homogenized for an additional 30-60 minutes after all of the drug was dissolved to ensure a homogenous solution. The product was then filtered through 5 micron Meissner Filter and all filtered material was collected. The product was vacuum deaerated for not less than an hour and until no air bubbles were observed. The product was encapsulated, dried and inspected visually to remove leakers, odds, under fills, and stickiness.

Example 3

Oral Bioavailability of Rigosertib

A Phase 1 study was conducted to assess oral bioavailability of a novel oral ON 01910.Na (Rigosertib) soft gelatin capsule formulation of Example 1 in MDS patients under fasted and fed conditions. This was a single-dose, three-treatment, three-period sequential design for studying the effects of food on the bioavailability of an immediate-release soft gelatin capsule formulation. The following dosing groups were tested in 12 patients: IV Dose 800 mg over 24 hours and oral dose 560 mg (2×280 mg capsules) under fasting and fed conditions. Plasma samples were collected pre-dose, over 32 hours (IV dose) or 8 hours (oral dose) after dose initiation. Rigosertib plasma levels were analyzed by a validated LC/MS/MS method. Pharmacokinetic parameters were estimated by non-compartmental analysis (WinNonlin®). Rigosertib pharmacokinetic parameters are presented in Table 1.

TABLE 1

Pharmacokinetic Characteristics of Rigosertib

| Parameter | Dosing Group | | |
|---|---|---|---|
| | 800 mg IV (24 hr infusion) | 560 mg Oral (Fasting) | 560 mg Oral (Fed) |
| $C_{max}$ (μg/ml) | 3.14 ± 1.13 | 2.42 ± 1.26 | 0.56 ± 0.31 |
| AUC (μg-hr/ml) | 52.7 ± 19.2 | 6.89 ± 3.98 | 2.71 ± 1.51 |
| $T_{max}$ (hr) | 2.91 ± 1.30 | 1.00 ± 0.45 | 2.82 ± 1.15 |
| $t_{1/2}$ (hr) | 3.25 ± 0.97 | 2.79 ± 1.23 | 2.61 ± 0.93 |
| Bioavailability (%) | N/A | 34.9 ± 17.6 | 13.8 ± 6.04 |

As seen from Table 1, the results demonstrated good oral bioavailability under fasting condition. Oral administration of Rigosertib after a meal decreased C. and AUC by 77% and 61%, respectively, as compared to fasting conditions. The results from the data in Table 1 clearly supported the potential for oral delivery of Rigosertib as a preferred therapy over a 3-day continuous intravenous infusion.

Example 4

Efficacy of ON 01910.Na in Cancer Therapy Refractory Patients

Safety and efficacy of a novel oral formulation of ON 01910.Na were determined in a dose escalation study in MDS patients refractory to ESA, lenalidomide and DNA Methyltransferase inhibitors.

ESA was allowed as concomitant medication. The drug dose was escalated based on a defined escalation dose scheme (70, 140, 280, 560, and 700 mg). The drug was administered orally twice a day for 14 days of a 21 day cycle. Pharmacokinetic dose proportionality was established in the 70-700 mg single dose range in the first 3 patients, and pharmacodynamically active concentrations were reached as shown in FIGS. 1A, 1B and 1C, respectively. The results show that the formulation was well tolerated. One patient experienced dose limiting toxicity (DLT) at the 700 mg dose level during the first 3-week cycle (dysuria and shortness of breath). Another patient at this dose level had a grade 3 dysuria during cycle 2. The results showed that 560 mg bid as the safe and efficacious dose. FIG. 2 shows that pharmacodynamically relevant levels of CyclinB1, p-Cdk1 and p-H3 were achieved with ON 01910.Na in In vitro experiments conducted in MDS cells.

Example 5

Rigosertib (ON 01910.Na) Hematological Effects in Patients with MDS and Correlation with Overall Survival In this Example, bone marrow (BM) response and overall survival (OS) were analyzed in 60 patients (pts) with MDS, including 51 patients with refractory anemia and excess blasts (RAEB) and 9 patients with refractory cytopenia and multilineage dysplasia (RCMD) enrolled in 4 independent Phase 1/II clinical trials. The results of this study are demonstrated in FIGS. 7 and 8.

The patients were treated with Rigosertib administered as a continuous intravenous infusion (CIV) from 2 to 6 days weekly or every other week with BM response initially assessed per protocol by week 4 or 8 and every 8 weeks thereafter. Overall survival (OS) analyses were performed by the method of Kaplan-Meier. OS was related (p=0.01) to FAB/WHO classification (see Table 2) in all MDS patients. Nine patients had hematological improvements. OS was also related to BM blastic response (Table 3; p=0.01) in the 51 RAEB-1,-2,-t patients and in a subset of 39 RAEB-1,-2,-t patients refractory or relapsing after treatment with hypomethylating agents (azacitidine/decitabine) (Table 3; p=0.003).

Forty seven (47%) of 15 patients in this last group treated with 3-day Rigosertib infusions (1800 mg/day) every other week were still alive at 49 weeks. Rigosertib infusions were well tolerated without evidence of bone marrow myelotoxicity. These results and the predictive value of BM response to Rigosertib for estimating OS survival have led to the initiation of a randomized Phase III survival trial of Rigosertib 3-day CIV infusions vs best supportive care in RAEB-1 (5-9% bone marrow blasts) RAEB-2 (10-20% bone marrow blasts) and -t (patients who failed or progressed after receiving hypomethylating agents.

TABLE 2

Overall Survival by FAB/WHO Classification in 60 MDS patients

| | FAB/WHO Classification | | | | |
|---|---|---|---|---|---|
| | RCMD | RAEB-1 | RAEB-2 | RAEB-T | P Value |
| N patients | 9 | 17 | 21 | 13 | |
| Median OS (weeks) | 98 | 43 | 37 | 20 | 0.01 |

TABLE 3

Overall Survival by BM Blast Response in 51 RAEB-1, 2, t-pts

| | BM Blast Response | | | | |
|---|---|---|---|---|---|
| | ≥50% Blast Decrease | Stable BM Response | Progressive Disease | Not Assessed | P Value |
| N patients | 16 | 21 | 4 | 10 | |
| Median OS (weeks) | 48 | 36 | 13.5 | 11 | 0.01 |

TABLE 4

Overall Survival by BM Blast Response in 39 RAEB-1, 2, t-pts Refractory or Relapsing After Azacitidine/Decitabine Treatment

| | BM Blast Response | | | | |
|---|---|---|---|---|---|
| | ≥50% Blast Decrease | Stable BM Response | Progressive Disease | Not Assessed | P Value |
| N patients | 13 | 14 | 3 | 9 | |
| Median OS (weeks) | 44 | 40 | 10 | 11 | 0.003 |

Example 6

Rigosertib-Mediated Inhibition of PI3K and PLK1 Pathways Validated in Patient Bone Marrow Samples Rigosertib (ON 01910.Na) was used in five clinical trials for myelodysplastic syndrome (MDS) in both intravenous and oral formulations. Results of bone marrow blast response and overall survival in 60 patients with MDS treated with intravenous Rigosertib were reported from four Phase I/II trials. A substantial proportion of patients had clinically significant reduction or stabilization in blasts (cancerous cells) and a correlation was evident between blast reduction and overall survival benefit. Rigosertib infusion showed no evidence of bone marrow toxicity. Based on these studies a randomized Phase III survival trial of Rigosertib treatment in higher-risk MDS patients who have failed or progressed after receiving hypomethylating agents was conducted. In a phase 1 evaluation of the oral formulation, results indicated that a pharmacodynamically effective drug level was achieved in MDS patients who were administered the Rigosertib capsule formulation. Signs of clinical activity were observed, including two cases of bone marrow responses in higher-risk patients refractory to hypomethylating agents, reduced needs for red cell transfusions in low-risk, transfusion-dependent patients, and transition to transfusion independence in some patients. The results are tabulated in Tables 5-6 below.

TABLE 5

Patients Characteristics

| PID | Age | Sex | Cytog | Prior Aza/Dec | Prior Lenalinomide | DOT (wks) | Ongoing | IPSS | Dose (mg) |
|---|---|---|---|---|---|---|---|---|---|
| 10 | 66 | M | +mar3 | Yes | | 6.5 | N | 1 | 560 |
| 12 | 73 | M | -7 | Yes | | 5 | N | 1 | 700 |
| 16 | 54 | M | Normal | Yes | | 11 | N | 1 | 700 |
| 31 | 81 | M | Normal | Yes | | 2 | N | 1 | 560 |
| 13 | 80 | M | Complex | Yes | | 13 | N | 1 | 700 |
| 14 | 64 | F | Complex | No | | 5 | N | Low | 700 |
| 18 | 81 | M | Complex | Yes | Yes | 19 | N | Low | 560 |
| 19 | 73 | M | Normal | No | Yes | 31 | Y | Low | 560 |
| 21 | 72 | F | Normal | Unk | | 29 | Y | Low | 560 |
| 24 | 58 | F | Normal | No | No | 22 | Y | 1 | 560 |
| 27 | 76 | M | Normal | Yes | | 9 | N | 1 | 560 |
| 29 | 85 | M | Not Done | Yes | Yes | 18 | Y | 1 | 560 |
| 34 | 57 | F | Normal | No | Yes | 16 | Y | Low | 560 |
| 35 | 58 | M | Normal | No | | 16 | Y | 1 | 560 |
| 36 | 80 | M | Normal | No | | 15 | Y | 1 | 560 |
| 39 | 64 | F | 3 Trans | No | | 11 | Y | 1 | 560 |

PID Nos 18, 19, 24 and 34 as highlighted in green are patients who achieved transfusion independence.
PID No 29 highlighted in orange shows erythroid response

TABLE 6

Transfusion independence and erythroid response

| TX response | Concomitant ESA | DOT (wks) | # Units pre 56ds | # Units during Trt | # Units/56 ds Trt | Onset Tx indep week | Duration Tx indep | Red RBC Units | % Reduction |
|---|---|---|---|---|---|---|---|---|---|
| NE* | | 6.5 | 6 | 4 | 4.9 | | | -1.1 | -18% |
| NE | | 5 | 6 | 4 | 6.4 | | | 0.4 | 7% |
| No | | 11 | 12 | 16 | 11.6 | | | -0.4 | -3% |
| NE | | 2 | 4 | 2 | 8.0 | | | 4.0 | 100% |
| No | Yes | 13 | 6 | 17 | 10.5 | | | 4.5 | 74% |
| NE | | 5 | 10 | 2 | 3.2 | | | -6.8 | -68% |
| TI | Yes | 19 | 6 | 10 | 3.1 | 10 | 16 | -2.9 | -49% |

TABLE 6-continued

Transfusion independence and erythroid response

| TX response | Concomitant ESA | DOT (wks) | # Units pre 56ds | # Units during Trt | # Units/56 ds Trt | Onset Tx indep week | Duration Tx indep | Red RBC Units | % Reduction |
|---|---|---|---|---|---|---|---|---|---|
| TI | Yes | 47 | 4 | 2 | 0.3 | 7 | 47+ | −3.7 | −87% |
| No | Yes | 29 | 8 | 16 | 4.4 | | | −3.6 | −45% |
| TI | Yes | 47 | 6 | 2 | 0.3 | 6 | 47+ | −5.7 | −88% |
| No | Yes | 9 | 8 | 13 | 11.6 | | | 3.6 | 44% |
| ER | Yes | 18 | 12 | 16 | 7.1 | | | −4.9 | −41% |
| TI | Yes | 16 | 4 | 4 | 2.0 | 3 | 8 | −2.0 | −50% |
| No | Yes | 16 | 10 | 21 | 10.5 | | | 0.5 | 5% |
| No | Yes | 15 | 6 | 8 | 4.3 | | | −1.7 | −29% |
| No | Yes | 11 | 6 | 4 | 2.9 | | | −3.1 | −52% |

*at least 8 wks Trt
TI: Highlighted in green shows patients who achieved transfusion independence.
ER: highlighted in orange shows erythroid response Example 7

Effect of Rigosertib (ON 01910.Na) in Patients with Relapsed or Refractory Acute Leukemia or Transformed Myeloproliferative Neoplasms In this Example a study in acute myeloid leukemia (AML) was initiated for investigating alternative schedules to determine the optimal dose and anti-leukemia efficacy. Results of a previous study showed that Rigosertib may be effective in myelodysplastic syndromes (MDS) patients who no longer respond to treatment with Vidaza (azacitidine) or Dacogen (decitabine).

To shed further light on the topic, data was analyzed from 31 MDS patients from four independent clinical trials in which the patients had failed treatment with Vidaza or Dacogen and subsequently received Rigosertib. Rigosertib was administered intravenously for two to six days every week or every other week. The patients' bone marrow was monitored for response to the treatment at week four or week eight and thereafter at an eight week interval.

Methods: The patients were >18 years of age with relapsed or refractory AML or transformed myeloproliferative neoplasms (MPN). Patients were given Rigosertib by continuous IV infusions over 24 hours with a fixed dose of 2400 mg/day either for 72 hrs or 120 hrs every other week using a standard dose escalation scheme. A blood sample was withdrawn at 6 hrs after the start of infusion during cycle 1 and cycle 2 to assess the plasma concentration of Rigosertib. The study was subsequently amended and, after 2 cycles of IV Rigosertib (each cycle being 2 weeks) patients received Rigosertib orally, 560 mg twice a day continuously for 20 weeks. The objectives of Phase I study were to define maximum tolerated dose (MTD), dose limiting toxicities (DLT), and identify all toxicities and anti-leukemia activity. Phase II primary objective was to determine the clinical efficacy; secondary objectives were to assess time to response or progression, duration of response and overall survival at 6 months.

Results: 26 patients have been enrolled in study median age was 66 years (range: 32-83 yrs) and 15 of them were males. Twenty patients were on a 72 hr dose schedule. The average plasma levels of Rigosertib in patients on week 1 and 3 were 9.20±5.05 and 9.81±6.70 µM, respectively. Eight patients were enrolled in phase 2. Diagnosis included: 10 (38%) de novo AML, 11 (42%) MDS related AML, 3 (12%) treatment related AML and 2 (8%) transformed MPN. Patients had received a median of 3 prior therapies (range: 1 to 7). There are 7 (27%) patients with primary refractory AML and 19 (73%) with relapsed AML. Seven of 26 (27%) patients had a prior allogeneic stem cell transplant and 50% had a complex karyotype. Patients received a median of 2 cycles (range, 1 to 4). The MTD was determined to be 2400 mg over 24 hrs for 3 days. In terms of efficacy, after 2 cycles best response noted is stabilization of disease with >50% absolute reduction of peripheral blasts in 2/25 (8%) patients, while in 4(16%) other patients peripheral blasts were maintained at +/−10% of pretreatment level. There was also transient hematologic response with improvement of platelets in another 4 (16%) patients.

In conclusion, progression of Phase I/II study of Rigosertib showed that it had an acceptable toxicity profile with the main adverse event (AE) being transient AMS (Altered mental status). Rigosertib therapy resulted in stable disease in some patients.

Example 8

Phase I/II Results of Rigosertib (ON 01910.Na) Hematological Effects in Patients with Myelodysplastic Syndrome and Correlation with Overall Survival The study evaluated the effectiveness of the oral formulation of Rigosertib in reducing the transfusion needs of transfusion-dependent lower-risk MDS patients. Results of bone marrow blast response and overall survival in 60 patients with MDS treated with intravenous Rigosertib were reported from four Phase I/II trials. A substantial proportion of patients had clinically significant reduction or stabilization in blasts (cancerous cells) and a correlation was evident between blast reduction and overall survival benefit. Rigosertib infusion showed no evidence of bone marrow toxicity. Based on these studies a randomized Phase III survival trial of Rigosertib treatment in higher-risk MDS patients who have failed or progressed after receiving hypomethylating agents is being conducted.

An oral dosage form of Rigosertib has completed a Phase I dose escalation trial in MDS patients. Pharmacodynamically relevant drug levels were achieved in MDS patients with Rigosertib capsule formulation. Signs of clinical activity were observed, including two cases of bone marrow responses in higher-risk patients refractory to hypomethylating agents, reduced needs for red cell transfusions in low-risk, transfusion-dependent patients, and transition to transfusion independence in some patients. Based on these results, Phase II studies were conducted in Low or Intermediate-1 risk, transfusion-dependent MDS patients.

Example 9

Intravenous Infusion of Rigosertib

Patients with relapsed or refractory AML or transformed myeloproliferative neoplasms (MPN) were given Rigosertib by continuous IV infusions over 24 hours (hrs) with a fixed dose of 2400 mg/day either for 72 hrs or 120 hrs every other week using a standard dose escalation scheme. A blood sample was withdrawn at 6 hrs after the start of infusion during cycle 1 and cycle 2 to assess the plasma concentration of Rigosertib. The study was subsequently amended and, after 2 cycles of IV Rigosertib (each cycle being 2 weeks) patients received Rigosertib orally, 560 mg twice a day continuously for 20 weeks. The objectives of phase 1 study were to define maximum tolerated dose (MTD), dose limiting toxicities (DLT), identify all toxicities and anti-leukemia activity. Phase 2 primary objective was to determine the clinical efficacy; secondary objectives were to assess time to response or progression, duration of response and overall survival at 6 months.

Results: 26 patients were enrolled in this study with median age of 66 yrs (range: 32-83 yrs), 15 of them being male. Twenty patients were on 72 hrs dose schedule. The average plasma levels of Rigosertib in patients on week 1 and 3 were 9.20±5.05 and 9.81±6.70 µM, respectively. In phase 2, patients had received a median of 3 prior therapies. There were 27% of patients with primary refractory AML, 73% of patients with relapsed AML, 27% of patients had a prior allogeneic stem cell transplant and 50% had a complex karyotype. The MTD was determined to be 2400 mg over 24 hrs for 3 days. DLT was at 2400 mg over 24 hrs. In terms of efficacy, after 2 cycles best response noted was the stabilization of disease with >50% absolute reduction of peripheral blasts. There was also transient hematologic response with improvement of platelets in some other patients. In conclusion, interim analysis of Phase I/II study of Rigosertib showed that it had an acceptable toxicity profile while providing disease stability.

Example 10

Effect of Rigosertib on Refractory Solid Tumors

Twenty-five patients with histologically confirmed solid tumors refractory to standard therapy were given escalating doses of oral Rigosertib twice daily. Doses were increased according to a schedule until the appearance of grade 2 or grade 3/4 toxicities. The maximum tolerated dose (MTD) of oral Rigosertib administered twice daily continuously is 560 mg BID. Dysuria was identified as a potential dose-limiting adverse event and a reported toxicity. The investigators found that dysuria could be successfully managed by ensuring oral hydration and administering sodium bicarbonate. The antitumor activity in this study supported past observations of Rigosertib efficacy in other solid tumor clinical trials. Pharmacokinetic (PK) data reveal plasma levels with oral Rigosertib were above the predicted pharmacodynamically active levels. Final safety and efficacy results, plasma and urinary PK relationships, and mutational analyses from archival tissue are presented Example 11

Phase II Study of Orally Administered Rigosertib in Transfusion-Dependent Lower Risk Myelodysplastic Syndrome (MDS) Patients Methods: This is a randomized, two-arm study of oral Rigosertib (560 mg bid) administered either intermittently (2 out of 3 weeks) or continuously. Transfusion-dependent patients received at least 4 units RBC transfusions over 8 weeks before randomization as well as transfusions and erythrocyte stimulating agents (ESAs) while on study.

Results: Twenty nine MDS patients (25 intermediate-1 and 4 low risk per IPSS classification) were randomized. The Pre-treatment characteristic of patients enrolled in this study is shown in Table 7. Patients general Characteristics and demographics are presented in Table 8. * indicates prior RBC transfusions administered within the 8 weeks preceding the start of the study

TABLE 7

Transfusion Responders: Pre-treatment characteristics of patients in Phase II randomized two-arm study Patients Characteristics

| PID | IPSS | Cytogenetics | Prior Trt | Prior ESA | EPO mU/mL | Prior RBC* |
|---|---|---|---|---|---|---|
| 01-01 | 0.5 | -Y | Len | Yes | 51 | 4 |
| 01-02 | 0.5 | 18 abn | Len | Yes | 35 | 4 |
| 01-07 | 0.5 | Normal | No | Yes | 117 | 4 |
| 01-10 | 0 | Normal | No | Yes | 32 | 4 |
| 01-14 | 0.5 | Normal | Len | Yes | 51 | 4 |
| 01-20 | 0 | Normal | Len | No | 128 | 4 |
| 01-23 | 1 | -Y | No | Yes | 14 | 4 |
| 01-25 | 1 | Complex | No | No | 15 | 4 |
| 01-26 | 0.5 | del20q | Aza | Yes | 361 | 4 |
| 01-27 | 0 | Normal | Len | Yes | 31 | 4 |
| 01-35 | 1 | +8 | Aza | Yes | 47 | 4 |
| 01-37 | 0 | Normal | No | Yes | 236 | 4 |
| 01-39 | 0.5 | del13q | Aza/Len | Yes | 216 | 4 |

TABLE 8

Patients Characteristics and demographics

| Characteristic | N = 43 |
|---|---|
| Median Age, years (range) | 72 (54-84) |
| Male/Female | 25/18 |
| Median years from diagnosis (range) | 2 (0-12) |
| Median prior MDS therapies (range) | 1 (0-10) |
| Prior treatment with HM agents/Lenalidomide | 12/10 |
| Prior treatment with ESAs | 22 |
| IPSS Risk at Screen (Low/Int-1/Int-2) | 7/34/2 |
| ECOG PS (0/1/2) | 35/3/5 |
| FAB/WHO Classification | |
| Refractory Anemia | 11 |
| Refractory Cytopenia with Multiple Dysplasia | 25 |
| RAEB-1 | 6 |
| RAEB-2 | 1 |
| Cytogenetics (Normal/Tri8/del5q/Other) | 20/4/2/26 |

The study design in low or independent transfusion-dependent MDS patients: 43 patients enrolled and randomized 1:1 in two groups. The first group was administered 560 mg capsules BID in days 1-14 of 21 day cycle. The second group was administered 560 mg capsules BID in days 1-21 of 21 day cycle. Thereafter the transfusion independence and erythroid response was measured and only 9 patients were randomized to continuous dosing. The protocol was amended for the remaining 34 patients on intermittent dosing. The group enrolled in intermittent dosing demonstrated a higher ability for continued treatment as shown in FIG. 5.

Overall drug related adverse effect was much lower in the group that was dosed intermittently. Table 9 shows the result of adverse effect in this group.

TABLE 9

Adverse side effects

| SYMPTOM | INCIDENTS IN 34 PATIENTS DOSED INTERMITTENTLY | | |
|---|---|---|---|
| SEVERITY | GRADE 2 | GRADE 3 | TOTAL % |
| Urinary urgency | 12, 1 SAE | 0 | 35 |
| Hematuria or Cytitis | 1 | 5 | 18 |
| Fatigue | 5 | 0 | 15 |
| Nausea | 3 | 0 | 9 |
| Neutropenia | 2 | 2 | 6 |
| Diarrhea | 1 | 0 | 3 |
| Abdominal Pain/discomfort | 1 | 0 | 3 |
| Insomnia | 1 | 0 | 3 |

Urinary toxicity was mitigated by switching from continuous to intermittent dosing schedule and by dose reduction for grade 2+ urinary symptoms. In these cases 560 mg bid dosing was replaced with 560 mg am (30 min+ before breakfast) and 280 mg 2 hs+ after lunch and 30 min+ before dinner. Dysuria questionnaire (American Urological Association) was provided to all patients at baseline, 3 weeks and every 3 cycles thereafter and recommend for vigorous hydration and bicarbonate prn.

Overall oral Rigosertib was well tolerated except for a high incidence (5 of 9 patients) of grade 2+ urinary side effects (dysuria, hematuria, cystitis, and urinary urgency) in the continuous dosing arm. Accordingly, the protocol was amended to allow all patients to be treated with intermittent dosing, with option of dose interruption/reduction resulting in a much lower frequency of urinary side effects (4/20 patients with urinary grade 2+ toxicity). Fifteen patients (none of them with del5q cytogenetics) have been treated with intermittent dosing for at least 8 weeks. Seven (47%) patients achieved transfusion independence (no RBC transfusion for at least 8 consecutive weeks), which lasted 8 to 27+ weeks. Six of 7 responding patients were refractory to prior treatment with ESAs and 5 of these 7 patients received concomitant ESAs, suggesting an effect of Rigosertib on ESA resistance.

As demonstrated in FIG. 9, the results of this phase II study indicated that intermittent dosing of Rigosertib administered orally is well tolerated and active in producing transfusion independence in approximately 50% of transfusion dependent, lower risk MDS patients.

TABLE 10

Transfusion Responders - Outcomes (weeks)

| | Response week | | ESA Treatment week | |
|---|---|---|---|---|
| PID | Onset | Duration | Start | Stop |
| 01-01 | 1 | 48+ | 3 | 12 |
| 01-02* | 4 | 12 | 4 | 4 |
| 01-07* | 19 | 12 | 5 | 11 |
| 01-10* | 13 | 8 | 6 | 10 |
| 01-14 | 1 | 17 | 3 | 9 |
| 01-20 | 1 | 37+ | 1 | 1 |

TABLE 10-continued

Transfusion Responders - Outcomes (weeks)

| | Response week | | ESA Treatment week | |
|---|---|---|---|---|
| PID | Onset | Duration | Start | Stop |
| 01-23 | 1 | 9 | 10 | 22 |
| 01-25 | 1 | 28 | 14 | 22 |
| 01-26 | 1 | 30 | 14 | 14 |
| 01-27* | 24 | 8 | 21 | 21 |
| 01-35 | 14 | 17+ | No | No |
| 01-37 | 1 | 12 | 9 | 9 |
| 01-39 | 1 | 14+ | No | No |

*synergy with ESA

TABLE 11

Transfusion Responders: Pre-Treatment Characteristics

| PID | IPSS | Cytogenetics | Prior Trt | Prior ESA | EPO mU/mL | Prior RBC* |
|---|---|---|---|---|---|---|
| 01-01 | 0.5 | -Y | Len | Yes | 51 | 4 |
| 01-02 | 0.5 | 18 abn | Len | Yes | 35 | 4 |
| 01-07 | 0.5 | Normal | No | Yes | 117 | 4 |
| 01-10 | 0 | Normal | No | Yes | 32 | 4 |
| 01-14 | 0.5 | Normal | Len | Yes | 51 | 4 |
| 01-20 | 0 | Normal | Len | No | 128 | 4 |
| 01-23 | 1 | -Y | No | Yes | 14 | 4 |
| 01-25 | 1 | Complex | No | No | 15 | 4 |
| 01-26 | 0.5 | del20q | Aza | Yes | 361 | 4 |
| 01-27 | 0 | Normal | Len | Yes | 31 | 4 |
| 01-35 | 1 | +8 | Aza | Yes | 47 | 4 |
| 01-37 | 0 | Normal | No | Yes | 236 | 4 |
| 01-39 | 0.5 | del13q | Aza/Len | Yes | 216 | 4 |

MDS patients undergoing treatment with Rigosertib became transfusion independent. The results of transfusion independency are presented in FIGS. 7-9. Overall transfusion response of all patients, including both evaluable and itt (Intention to Treat) patients are presented in Table 12.

TABLE 12

Overall Transfusion Response

| Regimen | Responders |
|---|---|
| Continuous | 2 |
| Intermittent | 13 |
| Total | 15 |

Example 12

Phase II Study of Oral Rigosertib as a Single Agent Administered in Transfusion-Dependent Lower Risk MDS Patients The ongoing phase II trial 09-05 is designed to evaluate oral Rigosertib as a single agent in transfusion-dependent lower risk MDS patients. This trial is a randomized, two-arm study of oral Rigosertib (560 mg bid) administered either intermittently (2 out of 3 weeks) or continuously. Transfusion-dependent patients must have received at least 4 units of RBC transfusions over 8 weeks before randomization and can receive transfusions and erythrocyte stimulating agents (ESAs) while on study. Interim results from the trial based upon accrual of 59 of 60 patients from five clinical sites are presented below.

TABLE 13

Study Demographic For Lower Risk MDS Transfusion Dependent Patients
Demographics are reported below and are typical of a lower
risk MDS transfusion dependent patient population.

| Characteristic | N = 59 |
|---|---|
| Median Age, years (range) | 74 (54-86) |
| Male/Female | 40/19 |
| Median years from MDS diagnosis (range) | 2 (0-12) |
| Median number prior MDS therapies (range) | 2 (0-6) |
| Prior treatment with HM agents | 27 |
| Prior treatment with Lenalidomide | 20 |
| Prior treatment with ESAs or EPO > 500 mU/mL | 33 |
| Median pre-study EPO (mU/mL) (range) | 128 (14-11199) |
| Median# (range) RBC transfusions in 8 weeks prior study | 4 (4-11) |
| # patients with thrombocytopenia grade 3+ | 16 |
| # patients with neutropenia grade 3+ | 15 |
| # patients with anemia grade 3+ | 14 |
| IPSS risk at screen (Low/Int-1) | 11/46/2 |
| ECOG PS (0/1/2) | 41/11/6 |
| FAB/WHO Classification | |
| Refractory Anemia | 19 |
| Refractory Cytopenia with Multiple Dysplasia | 32 |
| RAEB-1 | 7 |
| RAEB-2 | 1 |
| Cytogenetics (Normal/Tri8/del5q/Other) | 28/7/3/21 |

TABLE 14

Efficacy Results

| | | Week Follow-Up | | | | |
|---|---|---|---|---|---|---|
| PID | Pretreatment | 15 | 30 | 45 | 60 | Response |
| 01-15 | 5 | | | | | |
| 01-16 | 10 | 10 | 9 | 5 | 5 | BMCR |
| 01-26 | 6 | 77 | | | | PD |
| 01-30 | 6 | 3 | | | | BMCRu |
| 01-40 | 7 | 4 | 4 | | | BMCR |
| 01-43 | 5 | | | | | |
| 02-11 | 9 | | | | | |
| 04-03 | 8 | | | | | |

Eight patients were classified as RAEB-1 (N=7) or RAEB-2. Bone marrow blast values (in %) are reported below. Out of four evaluable patients, three achieved bone marrow complete response according to IWG 2006 criteria (one patient had an unconfirmed response) and one progressed. Nine patients (8 treated for at least 8 weeks) were treated with continuous dosing and two achieved transfusion independence for 10 weeks and 18 weeks+. Of 36 patients on intermittent dosing treated for at least 8 consecutive weeks, 14 (39%) achieved transfusion independence (TI defined by no RBC transfusion for at least 8 consecutive weeks) lasting 8 to 73+ weeks (median not reached). Intent-to-treat analysis showed that 14/39 (36%) patients treated with intermittent dosing achieved TI. Thirteen of 16 responding patients received concomitant ESAs, suggesting an effect of Rigosertib on ESA resistance or synergy with ESA. The table below reports transfusion response in relation to prior and concomitant ESA treatment.

A strategy to address and mitigate urinary side effects was implemented for modification in dosing schedule (Rigosertib daily dosing of 560 mg AM and 280 mg PM) to minimize nocturnal symptoms of urinary urgency as well as dose reduction or interruption to manage grade 2+ urinary toxicity. Twelve patients received this new dosing regimen for a median duration of 6 weeks (range: 2-12 weeks). Only one patient developed grade 2 urinary toxicity, suggesting that this new dosing could result in greatly improved urinary tolerability.

In conclusion, in Phase II Lower-risk transfusion dependent MDS where 50% of patients were non del5q, there was a strong signal for transfusion independence. Also, a synergy between Rigosertib and ESA was found. In all these patients intermittent dosing in 2-3 weeks cycle was better tolerated than continuous dosing. Intermittent dosing treated for at least 8 consecutive weeks, 15 (45%) achieved transfusion independence (TI or no RBC transfusion for at least 8 consecutive weeks) lasting 8 to 53+ weeks (median=17 weeks). Intent-to-treat analysis showed 17/48 (35%) patients achieved TI.

All references cited herein, including patents, patent applications, and publications, are hereby incorporated by reference in their entireties, whether previously specifically incorporated or not.

The foregoing description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein. Those skilled in the art will recognize, or be able to ascertain using no more than routine experimentation, many equivalents to the embodiments of the invention described herein. Such equivalents are encompassed by the following claims.

What is claimed is:

1. A method of treating a patient suffering from a refractory myelodysplastic syndromes (MDS) that is refractory to erythropoiesis stimulating agent (ESA) comprising administering to the patient Rigosertib represented by Formula 1 and ESA,

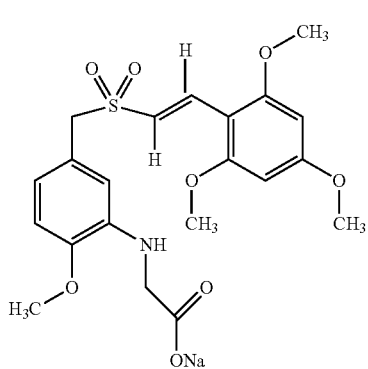

Formula 1 wherein combination of the Rigosertib and the ESA overcomes resistance to the ESA and causes transfusion independence in the patient.

2. The method of claim 1, wherein the administration of the Rigosertib is prior to, concomitant with, and/or after the administration of the ESA.

3. The method of claim 1, wherein the transfusion independence has achieved in the lower risk transfusion dependent patients in a phase II study.

4. The method of claim 1, wherein Rigosertib is administered orally, intravenously, or both.

5. The method of claim 1, wherein the ESA is administered to the patient prior to the administration of Rigosertib.

6. The method of claim 5, wherein the patients exhibit at least one symptom comprising refractory anemia and excess blasts (RAEB), cytopenia, multi-lineage dysplasia, reduced erythrocyte count, reduced platelet count, reduced hemoglobin concentration, or any combination thereof.

7. The method of claim 3, wherein Rigosertib is administered in an intermittent dosing for at least 8 weeks.

8. The method of claim 1, wherein Rigosertib is administered to the refractory MDS patients who had previously failed treatment with ESA and lenalidomide according to the following treatment schedule:

i) 560 mg oral Rigosertib twice daily for two to weeks intermittently; wherein the treatment results in a double increase in platelet values as compared to values obtained with ESA and lenalidomide alone.

9. The method of claim 1, wherein Rigosertib is administered orally and wherein a plasma peak level of Rigosertib in the patient after oral administration reaches at least 2-4 µM with a plasma half-life of about 10±0.5.

10. The method of claim 1, wherein:
a) Rigosertib is administered through continuous IV infusions over 24 hours with a fixed dose of 2400 mg/day either for 72 hours or 120 hours every other week using a standard dose escalation scheme,
b) Rigosertib is administered as a single-dose, three-treatment, in three-period of sequential administration under fasting conditions in an intravenous dose of 800 mg over 24 hours and an oral dose of 560 mg under fasting conditions, or
c) Rigosertib is administered orally with an intermittent dosing schedule of 560 mg/280 mg morning and afternoon, respectively for a period of 2-3 weeks.

* * * * *